United States Patent

Jeschke et al.

Patent Number: 5,529,984
Date of Patent: Jun. 25, 1996

[54] ENDOPARASITICIDAL COMPOSITIONS BASED ON OPEN-CHAIN HEXADEPSIPEPTIDES

[75] Inventors: Peter Jeschke, Leverkusen; Jürgen Scherkenbeck, Wermelskirchen; Andrew Plant, Odenthal; Achim Harder, Köln; Norbert Mencke, Leverkusen, all of Germany

[73] Assignee: Bayer Aktiengesellschaft, Leverkusen, Germany

[21] Appl. No.: 349,347

[22] Filed: Dec. 2, 1994

[30] Foreign Application Priority Data

Dec. 9, 1993 [DE] Germany .............. 43 41 991.7

[51] Int. Cl.$^6$ .............. A61K 38/15; C07K 11/00
[52] U.S. Cl. .............. 514/17; 514/18; 530/323; 930/30
[58] Field of Search .............. 514/17, 18; 530/323, 530/329, 331; 930/30

[56] References Cited

FOREIGN PATENT DOCUMENTS 4317458 12/1993 Germany .

OTHER PUBLICATIONS

Chemical Abstracts: Amino Acids, Peptides, Proteins vol. 121, 1994 p. 1247.
Tetrahedron Letters, No. 2, issued 1971, Ovchinnikov et al., "The Synthesis and Some Properties of Beauvericin", pp. 159–162.
H. G. Lerchen & H. Kunz: Tetrahedron Lett. 26 (43) pp. 5257–5260 (1985).
H. G. Lerchen & H. Kunz: Tetrahedron Lett. 28 (17) pp. 1873–1876 (1987).
B. F. Gisin: Helv. Chim. Acta 56 pp. 1476–1482 (1973).
R. Bowman et al: J. Chem. Soc., pp. 1346–1349 (1950).
J. R. McDermott et al: Can. J. Chem. 51 pp. 1915–1919 (1973).
E. Wurziger et al: Kontake [Catalysts] (Merck Darmstadt) 3 pp. 8–11 (1987).
S. M. Birnbaum et al: J. Amer. Chem. Soc. vol. 76 pp. 6054–6058 (1954).
C. S. Rondestvedt et al: Org. Reactions 11 pp. 189–260 (1960).

*Primary Examiner*—Jeffrey E. Russel
*Attorney, Agent, or Firm*—Sprung Horn Kramer & Woods

[57] ABSTRACT

This invention relates to a method of combatting endoparasites which comprises administering an endoparasiticidally effective amount of a hexadepsipetide of the formula

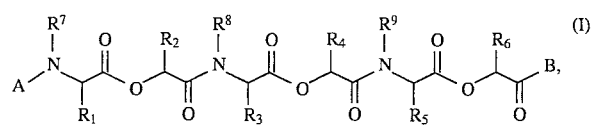

to a human or animal in need thereof.

3 Claims, No Drawings

ENDOPARASITICIDAL COMPOSITIONS BASED ON OPEN-CHAIN HEXADEPSIPEPTIDES

The present invention relates to the use of open-chain hexadepsipeptides for combating endoparasites.

Certain open-chain hexadepsipeptides as starting substances for endoparasiticidally active cyclic depsipeptides having 18 ring atoms (enniatins) are the subject-matter of an earlier, but not prior-published, patent application (German Patent Application P 4 317 458.2).

However, nothing has been disclosed as yet about a use of these compounds against endoparasites.

It has now been found that the open-chain hexadepsipeptides of the general formula (I)

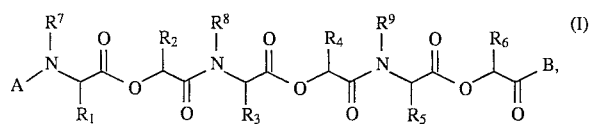

in which

A represents hydrogen, alkyl aralkyl or an acyl radical, in particular a radical of the formula —CO—$R^{10}$ in which $R^{10}$ represents straight-chain, branched alkyl, aralkyl, alkoxy or arylalkoxy having up to 6 carbon atoms in the alkyl moiety, $R^1$, $R^3$ and $R^5$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or represent alkoxycarbonylaminoalkyl, 9-fluorenylmethoxycarbonyl (Fmoc)aminoalkyl, alkenyl, cycloalkyl, cycloalkylalkyl, optionally substituted aryl, hetarylmethyl as well as arylalkyl, substituents which may be mentioned being halogen, hydroxyl, alkyl, alkoxy, nitro or a radical —$NR^{11}R^{12}$, where $R^{11}$ and $R^{12}$ independently of one another represent hydrogen or alkyl or $R^{11}R^{12}$ together with the adjacent N atom represent a carbocyclic 5-, 6- or 7-membered ring which can optionally also be interrupted by O, S and N and which is optionally substituted by $C_1$–$C_4$-alkyl, $R^2$, $R^4$ and $R^6$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkysulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, hetarylmethyl and optionally substituted arylalkyl, substituents which may be mentioned being halogen, hydroxyl, alkyl, alkoxy, nitro or a radical —$NR^{11}R^{12}$, where $R^{11}$ and $R^{12}$ independently of one another represent hydrogen or alkyl or $R^{11}R^{12}$ together with the adjacent N atom represent a carbocyclic 5-, 6- or 7-membered ring which can optionally also be interrupted by O, S and N and which is optionally substituted by $C_1$–$C_4$-alkyl, $R^7$, $R^8$ and $R^9$ independently of one another, represent hydrogen, $C_{1-8}$-alkyl, $C_{3-6}$-cydloalkyl or aralkyl, represents hydroxyl or alkoxy having up to 4 carbon atoms, and their optical isomers and racemates, can be used in medicine and veterinary medicine for combating endoparasires.

Formula (I) provides a general definition of the open-chain hexadepsipeptides to be used according to the invention. Compounds of the formula (I) which are preferably used according to the invention are those in which A represents hydrogen, $C_{1-4}$-alkyl, benzyl or a group of the formula —CO—$R^{10}$ in which $R^{10}$ represents straight-chain or branched $C_{1-4}$-alkyl, $C_{2-4}$-alkenyl, $C_{1-4}$-alkoxy or phenylalkoxy having up to 6 carbon atoms in the alkyl moiety, in particular tert-butoxy, benzyloxy, ethoxy, allyloxy, fluorenyl-9-methoxy or methoxy, $R^1$, $R^3$ and $R^5$ independently of one another represent hydrogen, straight-chain or branched $C_1$–$C_8$-alkyl, in particular methyl, ethyl, propyl, isopropyl, butyl, isobutyl, secbutyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tert-butoxycarbonylaminobutyl, 9-fluorenylmethoxycarbonyl (Fmoc)aminopropyl, 9-fluorenylmethoxycarbonyl (Fmoc)aminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, in particular phenyl, hetarylmethyl, in particular benzo[b]thien-1-yl-methyl, benzo[b]thien- 3-yl-methyl, naphth-1-yl-methyl, naphth-2-yl-methyl, pyrid-2-yl-methyl, pyrid-3-yl-methyl, fur-2-yl-methyl, fur-3-yl-methyl, thien-2-yl-methyl, thien-3-yl-methyl, indol-3-yl-methyl, N-methylindol- 3-yl-methyl, imidazol-4-yl-methyl, N-methyl-imidazol-4-yl-methyl, phenyl-$C_1$–$C_4$-alkyl, in particular phenylmethyl, which can optionally be substituted by radicals from the series comprising halogen, in particular fluorine, chlorine, bromine or iodine, hydroxyl, $C_1$–$C_4$-alkyl, in particular methyl or tertbutyl, $C_1$–$C_4$-alkoxy, in particular methoxy, ethoxy, methylenedioxy or ethylenedioxy, nitro or $C_1$–$C_4$-alkylamino, in particular methylamino, $C_1$–$C_4$-dialkylamino, in particular dimethylamino, $C_3$–$C_6$-cycloalkylamino, in particular piperidino or pyrrolidino, $C_3$–$C_6$-cycloalkoxyandno, in particular morpholino, $C_3$–$C_6$-cycloalkylthioxyamino, in particular thiomorpholino, $R^2$, $R^4$ and $R^6$ and independently of one another represent hydrogen, straight-chain or branched $C_1$–$C_8$-alkyl, in particular methyl, ethyl, propyl, isopropyl, butyl, isobutyl, secbutyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl, tertbutoxycarbonylaminobutyl, 9-fluorenylmethoxycarbonyl (Fmoc)aminopropyl, 9-fluorenylmethoxycarbonyl (Fmoc)aminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, in particular phenyl, hetarylmethyl, in particular benzo[b]thien-1-yl-methyl, benzo[b]thien-3-yl-methyl, naphth-1-yl-methyl, naphth-2-yl-methyl, pyrid-2-yl-methyl, pyrid-3-yl-methyl, fur-2-yl-methyl, fur-3-yl-methyl, thien-2-yl-methyl, thien-3-yl-methyl, indol-3-yl-methyl, N-methylindol-3-yl-methyl, imidazol-4-yl-methyl, N-methyl-imidazol-4-yl-methyl, phenyl-$C_1$–$C_4$-alkyl, in particular phenylmethyl, which can optionally be substituted by radicals from the series comprising halogen, in particular fluorine, chlorine, bromine or iodine, hydroxyl, $C_1$–$C_4$-alkyl, in particular methyl or tertbutyl, $C_1$–$C_4$-alkoxy, in particular methoxy, ethoxy, methylenedioxy or ethylenedioxy, nitro or $C_1$–$C_4$-alkylamino, in particular methylamino, $C_1$–$C_4$-dialkylamino, in particular dimethylamino, $C_3$–$C_6$-cycloalkylamino, in particular piperidino or pyrrolidino, $C_3$–$C_6$-cycloalkoxyamino, in particular morpholino, $C_3$–$C_6$-cycloalkylthioxyamino, in particular thiomorpholino, $R^7$, $R^8$ and $R^9$ independently of one another represent hydrogen, straight-chain or branched $C_1$–$C_4$-alkyl, in particular methyl, ethyl, isopropyl, t-butyl, s-butyl, benzyl, cyclopropyl or cyclohexyl, B represents hydroxyl or tert-butyloxy, and their optical isomers and racemates.

Compounds of the formula (I) which are particularly preferably used according to the invention are those in which A represents hydrogen or benzyl, or represents a group of the formula —CO—$R^{10}$, in which $R^{10}$ represents straight-chain or branched alkoxy or arylalkoxy having up to 6 carbon atoms in the alkyl moiety, in particular tert-butoxy or benzyloxy, $R^1$, $R^3$ and $R^5$ independently of one another represent hydrogen, straight-chain or branched $C_1$–$C_8$-alkyl, in particular methyl, ethyl, propyl, isopropyl, butyl, isobutyl, secbutyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylamino butyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, in particular phenyl, hetarylmethyl, in particular naphth-1-yl-methyl, pyrid-2-yl-methyl, pyrid-3-yl-methyl, thien-2-yl-methyl, thien-3-yl-methyl, indol-3-yl-methyl, N-methyl-indol-3-yl-methyl, imidazol-4-yl-methyl, N-methyl-imidazol-4-yl-methyl, phenyl-$C_1$–$C_4$-alkyl, in particular phenylmethyl, which can optionally be substituted by one or more identical or different radicals from amongst those mentioned above, $R^2$, $R^4$ and $R^6$ independently of one another represent hydrogen, straight-chain or branched $C_1$–$C_8$-alkyl, in particular methyl, ethyl, propyl, isopropyl, butyl, isobutyl, secbutyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonyl aminopropyl, tert-butoxycarbonylamino butyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, in particdlar phenyl, hetarylmethyl, in particular benzo[b]thien-2-yl-methyl, naphth-1-yl-methyl, naphth-2-yl-methyl, pyrid-2-yl-methyl, pyrid-3-yl-methyl, fur-2-yl-methyl, fur-3-yl-methyl, thien-2-yl-methyl, thien-3-yl-methyl, phenyl-$C_1$–$C_4$-alkyl, in particular phenylmethyl, which can be optionally substituted by one or more identical or different radicals from amongst those mentioned above, $R_7$, $R^8$ and $R^9$ independently of one another represent hydrogen, methyl, benzyl or cyclopropyl, B represents hydroxyl or tert-butyloxy, and their optical isomers and racemates.

Compounds of the formula (I) which are very particularly preferably used according to the invention are those in which A represents hydrogen, benzyl, tert-butyloxycarbonyl (Boc) or benzyloxycarbonyl (Z), R¹, R³ and R⁵ independently of one another represent hydrogen, straight-chain or branched $C_1$–$C_8$-alkyl, in particular methyl, ethyl, propyl, isopropyl, butyl, isobutyl, secbutyl, pentyl, isopentyl, sec-pentyl, hexyl, isohexyl, sec-hexyl, heptyl, isoheptyl, sec-heptyl, octyl, isooctyl, secoctyl, $C_2$–$C_8$-alkenyl, in particular allyl, $C_3$–$C_7$-cycloalkyl-$C_1$–$C_4$-alkyl, in particular cyclohexylmethyl, phenyl-$C_1$–$C_4$-alkyl, in particular phenylmethyl, R², R⁴ and R⁶ independently of one another represent hydrogen, straight-chain or branched $C_1$–$C_8$-alkyl, in particular methyl, ethyl, propyl, isopropyl, butyl, isobutyl, secbutyl, pentyl, isopentyl, sec-pentyl, hexyl, isohexyl, sec-hexyl, heptyl, isoheptyl, sec-heptyl, octyl, isooctyl, secoctyl, $C_2$–$C_8$-alkenyl, in particular vinyl, allyl, $C_3$–$C_7$-cycloalkyl-$C_1$–$C_4$-alkyl, in particular cyclohexylmethyl, phenyl-$C_1$–$C_4$-alkyl, in particular phenylmethyl, which can optionally be substituted by one or more identical or different radicals from amongst those mentioned above, R⁷, R⁸ and R⁹ represent methyl, B represents hydroxyl or tert-butyloxy, and their optical isomers and racemates.

The preparation of the open-chain hexadepsipeptides of the general formula (I) to be used according to the invention is the subject-matter of an earlier, but not prior-published, patent application by the applicant company (German Patent Application P 4 317 458-2).

The compoounds of the formula (I)

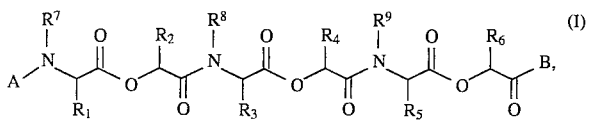

in which

A, R¹, R², R³, R⁴, R⁵, R⁶, R⁷, R⁸ and R⁹ and B have the meaning given further above, are obtained for example when a) tetradepsipeptides of the general formula (IIb)

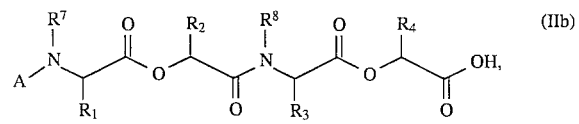

in which

A, R¹, R², R³, R⁴, R⁷ and R⁸ have the abovementioned meaning, are reacted with didepsipeptides of the general formula (VIc)

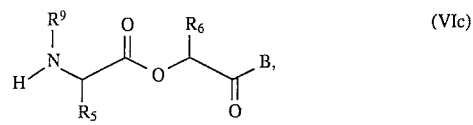

in which

B, R⁵, R⁶ and R⁹ have the meaning given further above, in the presence of suitable coupling reagents, in the presence of a basic reaction auxiliary and in the presence of a diluent, or b)tetradepsipeptides of the general formula (IIIc)

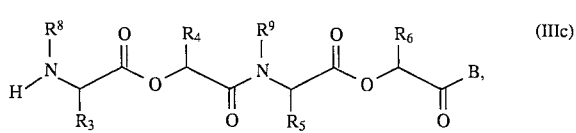

in which

B, R³, R⁴, R⁵, R⁶, R⁸ and R⁹ have the meaning given further above, are reacted with didepsipeptides of the general formula (IVb)

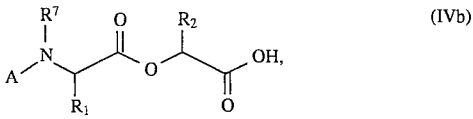

in which

A, R¹, R² and R⁷ have the meaning given further above, in the presence of suitable coupling reagents, in the presence of a basic reaction auxiliary and in the presence of a diluent.

The compounds of the general formula (I) can exist, and be used, in optically active, stereoisomeric forms or in the form of racemic mixtures. However, the optically active, stereoisomeric forms in compound of the general formula (I) are preferably used according to the invention.

The following contoounds of the general formula (I) in which the radicals R⁷ to R⁹ represent methyl and the radicals A, R¹ to R⁶ and B have the following meaning:

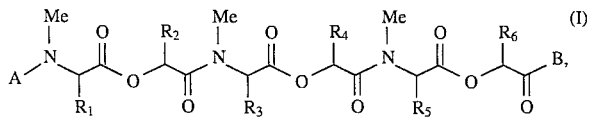

may be mentioned individually.

| A | R¹ | R² | R³ | R⁴ | R⁵ | R⁶ | B |
|---|---|---|---|---|---|---|---|
| —Bn | —CH₂—Ph | —CH₂—Ph | —CH₂—Ph | —Me | —CH₂—Ph | —CH₂—Ph | —O$^t$Bu |
| —Z | —CH₂—Ph | —CH₂—Ph | —CH₂—Ph | —Me | —CH₂—Ph | —CH₂—Ph | —O$^t$Bu |
| —H | —CH₂—Ph | —CH₂—Ph | —CH₂—Ph | —Me | —CH₂—Ph | —CH₂—Ph | —O$^t$Bu |
| —Bn | —CH₂—Ph | —CH₂—Ph | —CH₂—Ph | —Me | —CH₂—Ph | —CH₂—Ph | —OH |
| —Z | —CH₂—Ph | —CH₂—Ph | —CH₂—Ph | —Me | —CH₂—Ph | —CH₂—PH | —OH |
| —H | —CH₂—Ph | —CH₂—Ph | —CH₂—Ph | —Me | —CH₂—Ph | —CH₂—Ph | —OH |
| —Bn | —CH₂—Ph | —CH₂—Ph | —CH₂—Ph | —CH₂—Ph | —CH₂—Ph | —CH₂—Ph | —O$^t$Bu |
| —Z | —CH₂—Ph | —Me | —CH₂—Ph | —CH₂—Ph | —CH₂—Ph | —CH₂—Ph | —O$^t$Bu |
| —H | —CH₂—Ph | —Me | —CH₂—Ph | —CH₂—Ph | —CH₂—Ph | —CH₂—Ph | —O$^t$Bu |
| —Bn | —CH₂—Ph | —Me | —CH₂—Ph | —CH₂—Ph | —CH₂—Ph | —CH₂—Ph | —OH |
| —Z | —CH₂—Ph | —Me | —CH₂—Ph | —CH₂—Ph | —CH₂—Ph | —CH₂—Ph | —OH |
| —H | —CH₂—Ph | —Me | —CH₂—Ph | —CH₂—Ph | —CH₂—Ph | —CH₂—Ph | —OH |
| —Bn | —CH₂—Ph | —CH₂—Ph | —CH₂—Ph | —CH₂—Ph | —CH₂—Ph | —Me | —O$^t$Bu |
| —Z | —CH₂—Ph | —CH₂—Ph | —CH₂—Ph | —CH₂—Ph | —CH₂—Ph | —Me | —O$^t$Bu |
| —H | —CH₂—Ph | —CH₂—Ph | —CH₂—Ph | —CH₂—Ph | —CH₂—Ph | —Me | —O$^t$Bu |
| —Bn | —CH₂—Ph | —CH₂—Ph | —CH₂—Ph | —CH₂—Ph | —CH₂—Ph | —Me | —OH |
| —Z | —CH₂—Ph | —CH₂—Ph | —CH₂—Ph | —CH₂—Ph | —CH₂—Ph | —Me | —OH |

-continued

| A | R¹ | R² | R³ | R⁴ | R⁵ | R⁶ | B |
|---|---|---|---|---|---|---|---|
| —H | —CH₂—Ph | —CH₂—Ph | —CH₂—Ph | —CH₂—Ph | —CH₂—Ph | —Me | —OH |
| —Z | —CH₂—Ph | —Me | —CH₂—Ph | —CH₂—Ph | —CH₂—Ph | —Me | —OtBu |
| —H | —CH₂—Ph | —Me | —CH₂—Ph | —CH₂—Ph | —CH₂—Ph | —Me | —OtBu |
| —Z | —CH₂—Ph | —Me | —CH₂—Ph | —CH₂—Ph | —CH₂—Ph | —Me | —OH |
| —H | —CH₂—Chx | —CH₂—Chx | —CH₂—Chx | —Me | —CH₂—Chx | —CH₂—Chx | —OtBu |
| —H | —CH₂—Chx | —CH₂—Chx | —CH₂—Chx | —Me | —CH₂—Chx | —CH₂—Chx | —OH |
| —H | —CH₂—Chx | —Me | —CH₂—Chx | —CH₂—Chx | —CH₂—Chx | —CH₂—Chx | —OtBu |
| —H | —CH₂—Chx | —Me | —CH₂—Chx | —CH₂—Chx | —CH₂—Chx | —CH₂—Chx | —OH |
| —H | —CH₂—Chx | —CH₂—Chx | —CH₂—Chx | —CH₂—Chx | —CH₂—Chx | —Me | —OtBu |
| —H | —CH₂—Chx | —CH₂—Chx | —CH₂—Chx | —CH₂—Chx | —CH₂—Chx | —Me | —OH |
| —H | —CH₂—Chx | —Me | —CH₂—Chx | —CH₂—Chx | —CH₂—Chx | —Me | —OtBu |
| —H | —CH₂—Chx | —Me | —CH₂—Chx | —CH₂—Chx | —CH₂—Chx | —Me | —OH |
| —Bn | —CHMeCH₂Me | —(CH₂)₂—Me | —CHMeCH₂Me | —Me | —CHMeCH₂Me | —(CH₂)₂—Me | —OtBu |
| —Z | —CHMeCH₂Me | —(CH₂)₂—Me | —CHMeCH₂Me | —Me | —CHMeCH₂Me | —(CH₂)₂—Me | —OtBu |
| —H | —CHMeCH₂Me | —(CH₂)₂—Me | —CHMeCH₂Me | —Me | —CHMeCH₂Me | —(CH₂)₂—Me | —OtBu |
| —Bn | —CHMeCH₂Me | —(CH₂)₂—Me | —CHMeCH₂Me | —Me | —CHMeCH₂Me | —(CH₂)₂—Me | —OH |
| —Z | —CHMeCH₂Me | —(CH₂)₂—Me | —CHMeCH₂Me | —Me | —CHMeCH₂Me | —(CH₂)₂—Me | —OH |
| —H | —CHMeCH₂Me | —(CH₂)₂—Me | —CHMeCH₂Me | —Me | —CHMeCH₂Me | —(CH₂)₂—Me | —OH |
| —Bn | —CHMeCH₂Me | —(CH₂)₃—Me | —CHMeCH₂Me | —Me | —CHMeCH₂Me | —(CH₂)₃—Me | —OtBu |
| —Z | —CHMeCH₂Me | —(CH₂)₃—Me | —CHMeCH₂Me | —Me | —CHMeCH₂Me | —(CH₂)₃—Me | —OtBu |
| —H | —CHMeCH₂Me | —(CH₂)₃—Me | —CHMeCH₂Me | —Me | —CHMeCH₂Me | —(CH₂)₃—Me | —OtBu |
| —Bn | —CHMeCH₂Me | —(CH₂)₃—Me | —CHMeCH₂Me | —Me | —CHMeCH₂Me | —(CH₂)₃—Me | —OH |
| —Z | —CHMeCH₂Me | —(CH₂)₃—Me | —CHMeCH₂Me | —Me | —CHMeCH₂Me | —(CH₂)₃—Me | —OH |
| —H | —CHMeCH₂Me | —(CH₂)₃—Me | —CHMeCH₂Me | —Me | —CHMeCH₂Me | —(CH₂)₃—Me | —OH |
| —Bn | —CHMe₂ | —CH₂—Ph | —CHMe₂ | —Me | —CHMe₂ | —CH₂—Ph | —OtBu |
| —Bn | —CH₂—Me | —CH₂—Ph | —CH₂—Me | —Me | —CH₂—Me | —CH₂—Ph | —OtBu |
| —Bn | —(CH₂)₂—Me | —CH₂—Ph | —(CH₂)₂—Me | —Me | —(CH₂)₂—Me | —CH₂—Ph | —OtBu |
| —Bn | —(CH₂)₃—Me | —CH₂—Ph | —(CH₂)₃—Me | —Me | —(CH₂)₃—Me | —CH₂—Ph | —OH |
| —Bn | —CHMeCH₂Me | —CHMeCH₂Me | —CHMeCH₂Me | —Me | —CHMeCH₂Me | —CHMeCH₂Me | —OH |
| —Bn | —CH₂—O—Bn | —Me | —CHMeCH₂Me | —Me | —CHMeCH₂Me | —CH₂—Ph | —OH |
| —H | —CH₂—OH | —CH₂—Ph | —CHMeCH₂Me | —Me | —CHMeCH₂Me | —CH₂—Ph | —OtBu |
| —H | —CH₂—OH | —CH₂—Ph | —CHMeCH₂Me | —Me | —CHMeCH₂Me | —CH₂—Ph | —OH |

Me = methyl; Chx = cyclohexyl; Phe = Phenyl; tBu = tertbutyl; Z = —CO—O—CH₂-phenyl; Bn = benzyl The depsipeptides which can be used according to the invention and their starting compounds can be prepared by traditional processes, for example by the process described by H.-G. Lerchen and H. Kunz (Tetrahedron Lett. 26 (43) (1985) pp. 5257–5260; 28 (17) (1987) pp. 1873–1876) utilizing the esterification process described by B. F. Gisin (Helv. Chim. Acta 56 (1973) p. 1476).

Some of the N-methyl-amino acids and 2-halogeno-carboxylic acid derivatives used as starting materials are known (cf. for example N-methyl-amino acids: R. Bowmann et al. J. Chem. Soc. (1950) p. 1346; J. R. McDermott et al. Can. J. Chem. 51 (1973) p. 1915; H. Wurzinger et al., Kontakte [Catalysts] (Merck. Darmstadt) 3 (1987) p. 8; 2-Halogeno-carboxylic Acid Derivatives: S. M. Birnbaum et al. J. Amer. Chem. Soc. 76 (1954) p. 6054, C. S. Rondestvedt, Jr. et al. Org. Reactions 11 (1960) p. 189. [Review]) or can be obtained by the processes described in these publications.

Coupling reagents which can be used for the coupling reaction to synthesize the depsipeptides (II), (III), (IV), (V) and (VI) employed as starting compounds are all coupling reagents suitable for producing an amide linkage (cf., for example, Houben-Weyl, Methoden der organischen Chemie [Methods in Organic Chemistry], Vol. 15/2; Bodanszky et al., Peptide Synthesis 2nd ed. (Wiley & Sons, New York 1976) or Gross, Meienhofer, The Peptides: Analysis synthesis, biology (Academic Press, New York 1979).

The open-chain hexadepsipeptides of the formula (I) in which the radicals $R^7$ to $R^9$ represent methyl and which are in accordance with the invention can therefore be obtained by the following reaction sequence:

a) Synthesis of the didepsipeptides of the formulae (IV) to (VI):

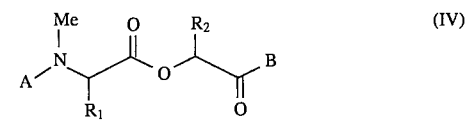
(IV)

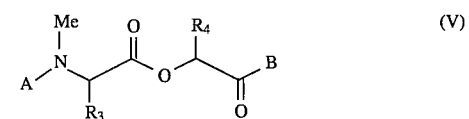
(V)

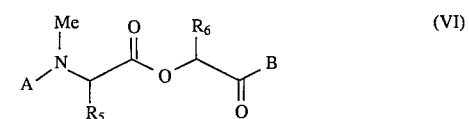
(VI)

in which A denotes an N-terminal protective group, such as, for example, the benzyl or benzyloxycarbonyl group, and B denotes a C-terminal protective group, such as, for example, the tert-butoxy group.

In the case of formula (VIa), for example, this follows the equation:

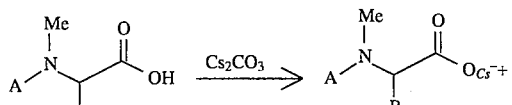

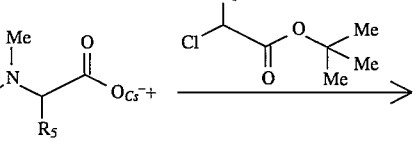

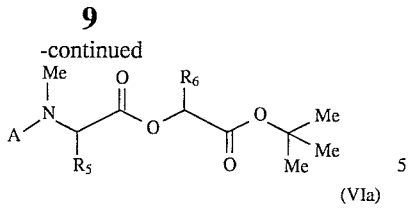

(VIa)

If appropriate, the preparation of the enantiomerically pure ccmtoounds of the formulae (IV), (V) and (VI) can also be effected via separation of the diastereomers by customary processes such as, for example, crystallization, by column chromatography or by countercurrent distribution. The best process will have to be worked out in each individual case; occasionally, it is also advantageous to use combinations of the individual,processes.

At the end of this step, it is either possible to remove the N-terminal protective group from the derivatives of the formula (VIa) in a manner known per se, for example by catalytic hydrogenation, to prepare the derivatives of the formula (VIc), or else it is possible to eliminate the C-terminal protective group from the derivatives of the formula (IV) and (V) in a manner known per se, for eyantole by acidolysis, to synthesize the derivatives (IVb) and (Vb):

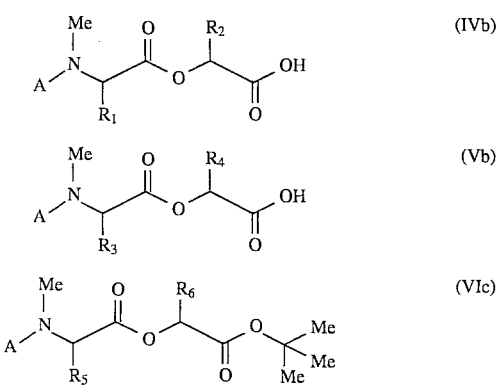

b) Synthesis of the tetradepsipeptides of the formula (II) and (III)

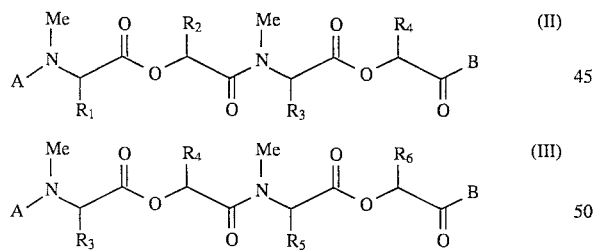

in the case of formula (IIIa), this follows the equation:

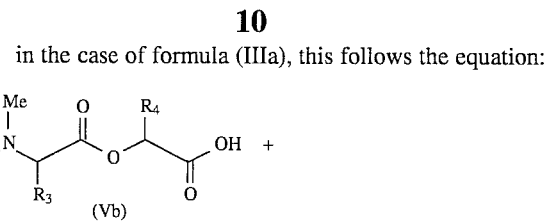

To prepare the derivatives of the formula (IIIc)

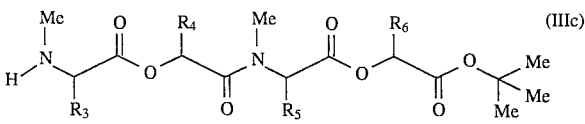

the N-terminal protective group can subsequently be eliminated from the derivatives of the formula (IIIa), for example by catalytic hydrogenation, as indicated above c) Synthesis of the open-chain hexadepsipeptides of the formula (I)

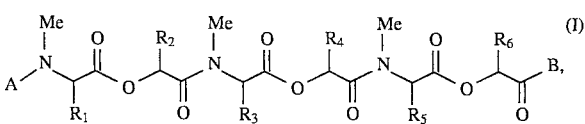

by the following equation:

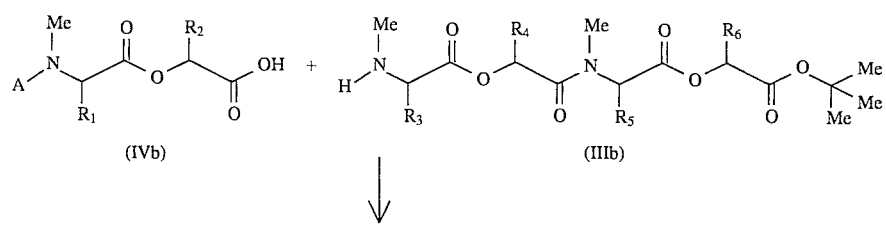

-continued

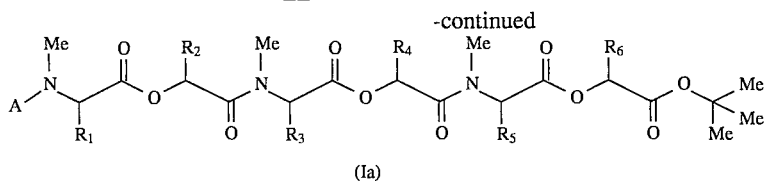

The C-terminal protective group can subsequently be eliminated from the derivatives of the formula (Ia) in a manner known per se, for example by acidolysis, to prepare the derivatives

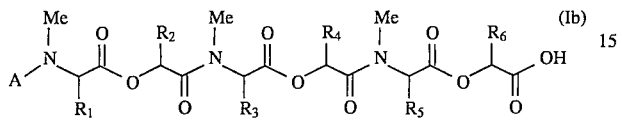

or the derivatives of the formula (Ia) are subjected to N-terminal deblocking in a manner known per se, for example by catalytic hydrogenation as indicated above, to prepare the derivatives of the formula (Ic)

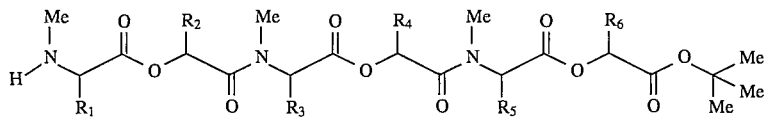

At the end of these steps, the N-terminal or C-terminal protective group can be eliminated from the derivatives of the formula (Ib) or (Ic), respectively, in a manner known per se, for example by catalytic hydrogenation or by acidolysis as indicated above, to prepare the derivatives of the formula (IId)

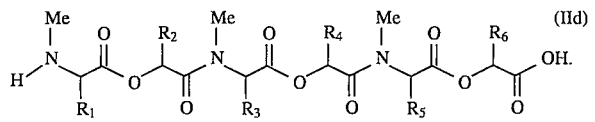

The products obtained can be purified in the customary manner by recrystallization or column chromatography (cf. also the Preparation Examples).

While having favourable toxicity to warm-blooded species, the active compounds are suitable for combating pathogenic endoparasites which occur in humans and in animal keeping and livestock breeding in productive livestock, breeding animals, zoo animals, laboratory animals, experimental animals and pets. They are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Grrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp. , Catatropis spp., Plagiorchis spp., Prosthogonimus spp. , Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostonmm spp., Cyclococercus spp., Cylicostephanus spp., Oesophagostonmm spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus slop., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The productive livestock and breeding animals include manmals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carp, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powder, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of injection (intramuscularly, subcutaneously, intravenously, intraperitoneally) or by implants.

Suitable preparations are:

Solutions such as solutions for injections, oral solutions, concentrates for oral administration after dilution, solutions for use on the skin or in body cavities, pour-on and spot-on formulations, gels;

Emulsions and suspensions for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol. Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on. These solutions are prepared as described above in the case of solutions for injection.

It may be advantageous to add thickeners during the preparation. Thickeners are: inorganic thickeners such as bentonire, colloidal silica, aluminium monostearate, organic thickeners such as cellulose derivatives, polyvinyl alcohols and their copolymers, acrylates and methacrylates.

Gels are applied to, or brushed on, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically. Pour-on and spot-on formulations are prepared by dissolving, suspending or emulsifying the active compound in suitable solvents or solvent mixtures which are tolerated by the skin. If appropriate, other adjuvants such as colourants, resorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colourants are all colourants which are released for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are gulphires or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colourants, resorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmirate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as Na-lauryl sulphate, fatty alcohol ether sulphates, the monoethynol amine salt of mono/dialkylpolyglycol ether orthophosphoric esters.

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methylvinyl ether and maleic anhydride, polyethylene glycols, waxes, colloidal silica, or mixtures of the substances mentioned.

Suspensions can be administered orally, dermally or in the form of injection. They are prepared by suspending the active substance in an excipient liquid, if appropriate with the addition of further adjuvants such as wetting agents, colourants, resorption accelerators, preservatives, antioxidants light stabilizers.

Excipient liquids which may be mentioned are all homogenous solvents and solvent mixtures.

Wetting agents (dispersants) which may be mentioned are the surfactants indicated further above.

Further adjuvants which may be mentioned are those indicated further above. Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, carcass meals, cereal meals and coarse cereal meals and starches.

Adjuvants are preservatives, antioxidants and colourants which have already been indicated further above.

Other suitable adjuvants are the lubricants and gliding agents such as, for example, magnesium stearate, stearic acid, talc, bentonires, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of 10 ppm—20 percent by weight, preferably of 0.1–10 percent by weight.

Preparations which are diluted prior to administration contain the active compound in concentrations of 0.5–90 percent by weight, preferably of 5–50 percent by weight.

In general, it has proved advantageous to administer amounts of approximately 1 to approximately 100 mg of active compound per kg of body weight per day to achieve effective results.

EXAMPLE A

In vivo nematode test

Haemonchus contortus/sheep

Sheep infected experimentally with Haemonchus contortus were treated after the prepatency period of the parasite had elapsed. The active compounds were administered orally and/or intravenously in the form of the pure active compound.

The degree of effectiveness is determined by quantitatively determining the nematode eggs excreted with the faeces before and after the treatment.

If egg excretion has stopped completely after the treatment, this means that the nematodes were aborted or are damaged to such an extent that they no longer produce eggs (Dosis effective).

Active compounds which have been tested and effective dosage rates (Dosis effective) can be seen from the table which follows:

| Active compound Example No. | Dosis effective in mg/kg |
| --- | --- |
| 3 | 10 |
| 6 | 10 |
| 14 | 10 |
| 43 | 10 |
| 52 | 10 |
| 63 | 10 |
| 65 | 10 |
| 67 | 10 |

Preparation Examples

EXAMPLE 1 tert-Butyl N-benzyloxycarbonyl-N-methyl-L-isoleucyl-D-lactyl-N-methyl-L-isoleucyl-D-lactyl-N-methyl-L-isoleucyl-D-lactate

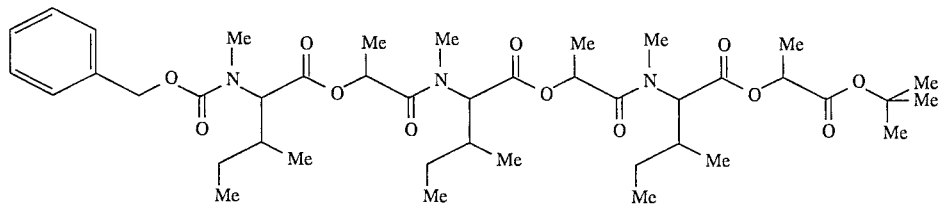

4.7 g (36.3 mmol) of N,N-diisopropylethylamine ("Hünig base") and 4.6 g (18.1 mmol) of bis(2-oxo-3-oxazolidinyl)-phosphinic chloride (BOP-Cl) are added at 0° C. to a solution of 5.8 g (16.5 mmol) of Z-L-MeIle-D-Lac-OH and 7.8 g (16.5 mmol) of H-(-L-MeIle-D-Lac-)$_2$—O—$^t$Bu in 150 ml of methylene chloride, and the mixture is stirred for 4 hours. The reaction solution is shaken twice with water, and the organic phase is separated off, dried and then concentrated in vacuo over sodium sulphate. The crude product which remains is chromatographed over a silica gel column (silica gel 60—Merck, mesh size: 0.04 to 0.063 mm) using toluene: ethyl acetate (5:1) as the eluent. 10.3 g (77.4% of theory) of tert-butyl N-benzyl-oxycarbonyl-N-methyl-L-isoleucyl-D-lactyl-N-methyl-L-isoleucyl-D-lactate-N-methyl-L-isoleucyl-D-lactate are obtained.

FAB-MS m/z (%): 805 (M$^+$,3); 749 (M$^+$—H$_2$C=CMe$_2$, 10); 732 (9); 793 (10); 91 (100)

EXAMPLE 2 tert-Butyl N-benzyl-N-methyl-L-isoleucyl-D-lactyl-N-methyl-L-isoleucyl-D-lactyl-N-methyl-L-phenylalanyl-D-lactate

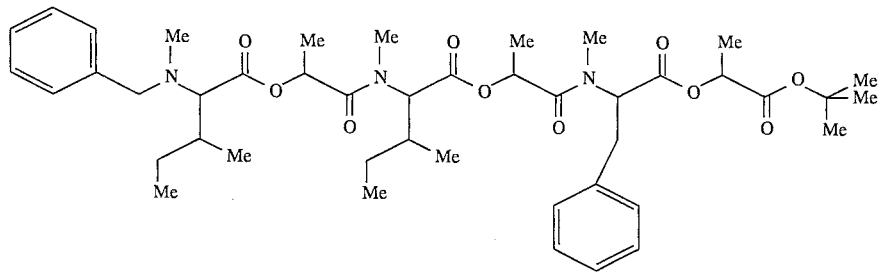

The coupling reaction is carried out analogously to the reaction protocol of Example 1, but:

7.4 g (14.6 mmol) of N-benzyl-N-methyl-L-isoleucyl-D-lactyl-N-methyl-L-isoleucyl-D-lactic acid, 4.5 g (14.6 mmol) of tert-butyl N-methy-L-phenylalanyl-D-lactate, 150 ml of methylene chloride, 4.1 g (32.2 mmol) of N, N-diisopropylethylamine ("Hünig base") and 4.1 g (16.1 mmol) of bis (2-oxo-3-oxazolidinyl)-phosphinic chloride (BOP-Cl)

are used. The crude product which remains is first chromatographed over a silica gel column (silica gel 60—Merck, mesh size: 0.04 to 0.063 mm) using toluene-:ethyl acetate (3:1) and methylene chloride:methanol (8:1) as the eluent and subsequently using toluene:ethyl acetate (10:1) as the eluent.

5.2 g (44.6% of theory) of tert-butyl N-benzyl-N-methyl-L-isoleucyl-D-lactyl-N-methyl-L-isoleucyl-D-lacyl-N-methyl-L-phenylalanyl-D-lactate are obtained.

EI-MS m/z (%): 794 (M$^+$,1); 297 (8); 190 (100)

EXAMPLE (II-2)

N-Benzyloxycarbonyl-N-methyl-L-isoleucyl-D-lactyl-N-methyl-L-isoleucyl-D-lactyl-N-methyl-n-isoleucyl-D-lactic acid

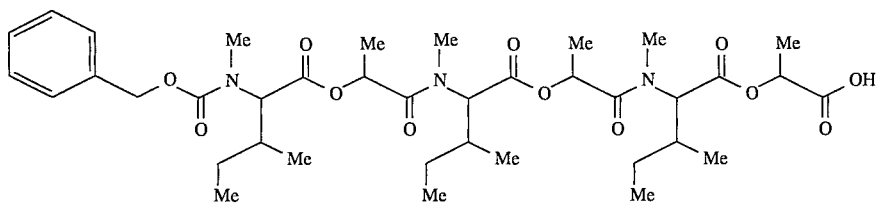

Dry hydrogen chloride gas is passed for 20 minutes into a solution, cooled to 0° C., of 9.2 g (11.2 mmol) of Z-(L-MeIle-D-Lac-)₃—O—ᵗBU in 150 ml of absolute methylene chloride. The mixture is subsequently stirred for approximately 16 hours at room temperature, and the entire reaction batch is concentrated in vacuo. 7.1 g (82.9% of theory) of N-benzyloxycarbonyl-N-methyl-L-isoleucyl-D-lactyl-N-methyl-L-isoleucyl-D-lactyl-N-methyl-L-isoleucyl-D-lactic acid are obtained.

MS m/z (%): 749 (M⁺, 10); 721 (1); 693 (2); 533 (0.5); 91 (100)

EXAMPLE 4 tert-Butyl N-methyl-L-leucyl-D-phenyllactyl-N-methyl-L-leucyl-D-phenyllactyl-N-methyl-L-leucyl-D-lactate

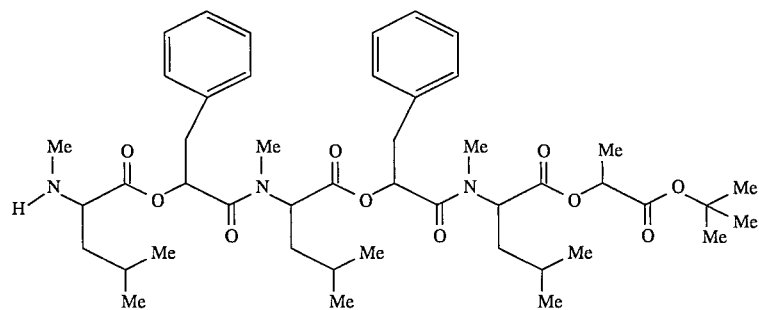

5.5 g (6.02 mmol) of Bn-L-MeLeu-D-PheLac-L-MeLeu-D-PheLac-MeLeu-D-Lac-OᵗBu are hydrogenated in 120 ml of ethanol in the presence of 0.6 g of Pd(OH)₂/charcoal [Pd content: 20%] until hydrogen is no longer taken up (approximately 4 hours). After the catalyst has been filtered off, the entire reaction solution is concentrated in vacuo. 4.8 g (97% of theory) of tert-butyl N-methyl-L-leucyl-D-phenyllactyl-N-methyl-D-phenyllactyl-N-methyl-L-leucyl-D-lactate are obtained.

EI-MS m/z (%): 808 (M⁺, 4); 680 (5); 624 (2); 462 (1); 348 (3); 259 (27); 100 (100)

EXAMPLE 5

N-Methyl-L-isoleucyl-D-lactyl-N-methyl-L-isoleucyl-D-lactyl-N-methyl-N-methyl-L-isoleucyl-D-lactic acid

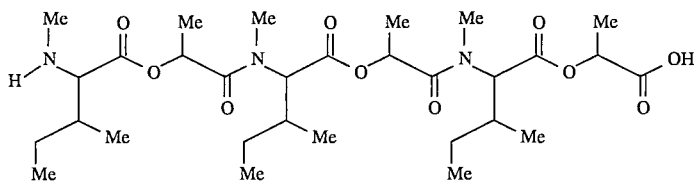

N-Terminal deblocking is carried out analogously to the reaction protocol of Example 4 in the course of approximately 2 hours, but 1.00 g (1.33 mmol) of N-benzyloxycarbonyl-N-methyl-L-isoleucinyl-D-lactyl-N-methyl-L-isoleucyl-D-lactyl-N-methyl-L-isoleucyl-D-lactic acid 0.15 g of pd(OH)₂/charcoal (Pd content: 20%) and 20 ml of ethanol are used.

0.81 g (100% of theory) of N-methyl-L-isoleucyl-D-lactyl-N-methyl-L-isoleucyl-D-lactyl-N-methyl-L-isoleucyl-D-lactic acid is obtained.

EI-MS m/z (%): 615 (M$^+$, 3); 600 (1); 558 (7); 472 (8); 386 (14); 100 (100

The compounds of the general formula (I; $R^7$ to $R^9$=—Me) listed in Table 1 below can be prepared analogously in the form of the LDLDLD stereoisomers.

TABLE 1

Examples of compounds of the formula (I; $R^7$ to $R^9$ = —Me)

| Ex. No. | A | $R^1$ | $R^2$ | $R^3$ | $R^4$ | $R^5$ | $R^6$ | B | Physical data[a] |
|---|---|---|---|---|---|---|---|---|---|
| 6 | —CO—O—CH$_2$—Ph | —CH$_2$CHMe$_2$ | —Me | —CH$_2$CHMe$_2$ | —Me | —CH$_2$CHMe$_2$ | —Me | —OH | 750 (M$^{30}$ + H); 706 (2); 461 (8); 91 (100) |
| 7 | —CO—O—CH$_2$Ph | —CH$_2$CHMe$_2$ | —Me | —CH$_2$CHMe$_2$ | —Me | —CH$_2$CHMe$_2$ | —Me | —O—CMe$_3$ | 805 (M$^+$, 1); 749 (M$^+$ — H$_2$C=CMe$_2$, 12); 91 (100) |
| 8 | —CO—O—CH$_2$Ph | —CH$_2$CHMe$_2$ | —Me | —CH$_2$CHMe$_2$ | —CH$_2$Ph | —CH$_2$CHMe$_2$ | —Me | —OH | 826 (M$^+$, 4); 769 (22); 690 (10); 91 (100) |
| 9 | —CO—O—CH$_2$Ph | —CH$_2$CHMe$_2$ | —Me | —CH$_2$CHMe$_2$ | —CH$_2$Ph | —CH$_2$CHMe$_2$ | —Me | —O—CMe$_3$ | 881 (M$^+$, 4); 825 (M$^+$ — H$_2$C=CMe$_2$, 16); 807 (7), 869 (14); 91 (100) |
| 10 | —CH$_2$Ph | —CHMeCH$_2$Me | —CHMe$_2$ | —CHMeCH$_2$Me | —Me | —CH$_2$Ph | —Me | —OH | 824 (M$^+$, 3); 766 (10; 704 (37); 190 (100) |
| 11 | —CH$_2$Ph | —CHMeCH$_2$Me | —CHMe$_2$ | —CHMeCH$_2$Me | —Me | —CH$_2$Ph | —Me | —O—CMe$_3$ | 879 (M$^+$, 5); 822 (10); 760 (21); 704 (14); 191 (100) |
| 12 | —CO—O—CH$_2$Ph | —CHMeCH$_2$Me | —CHMe$_2$ | —CHMeCH$_2$Me | —Me | —CH$_2$Ph | —Me | —O—CMe$_3$ | 867 (M$^+$, 8); 811 (12); 732 (10; 210 (100) |
| 13 | —CO—O—CH$_2$Ph | —CHMeCH$_2$Me | —CHMe$_2$ | —CHMeCH$_2$Me | —Me | —CH$_2$Ph | —Me | —O—CMe$_3$ | 923 (M$^+$, 1); 868 (8); 851 (6); 91 (100) |
| 14 | —H | —CH$_2$CHMe$_2$ | —Me | —CHMeCH$_2$Me | —Me | —CHMeCH$_2$Me | —Me | —OH | 615 (M$^+$, 5); 472 (5); 386 (17); 327 (7); 100 (100) |
| 15 | —CH$_2$Ph | —CH$_2$CHMe$_2$ | —Me | —CH$_2$CHMe$_2$ | —Me | —CHMeCH$_2$Me | —Me | —OH | 761 (M$^+$, 1), 688 (M$^+$ — OCMe$_3$, 4); |
| 16 | —CH$_2$Ph | —CH$_2$CHMe$_2$ | —Me | —CHMeCH$_2$Me | —Me | —CHMeCH$_2$Me | —Me | —OH | 642 (5); 586 (5); 190 (100) |
| 17 | —H | —CHMeCH$_2$Me | —CHMe$_2$ | —CHMeCH$_2$Me | —Me | —CHMeCH$_2$Me | —Me | —OH | 707 (M$^+$+ H, 60); 190 (100) |
| 18 | —CH$_2$Ph | —CHMeCH$_2$Me | —CHMe$_2$ | —CHMeCH$_2$Me | —Me | —CHMeCH$_2$Me | —Me | —OH | 790 (M$^+$, 1); 789 (M$^+$ — H, 1); 717 (M$^+$ — OCMe$_3$, 4); 770 (7); 190 (100) |
| 19 | —CH$_2$Ph | —CHMeCH$_2$Me | —CHMe$_2$ | —CHMeCH$_2$Me | —Me | —CHMeCH$_2$Me | —Me | —O—CMe$_3$ | 796 (M$^+$, 2), 795 (M$^+$-11, 6); 723 (M$^+$ — OCMe$_3$, 3); 704 (47); 224 (100) |
| 20 | —CH$_2$Ph | —CH$_2$Ph | —Me | —CHMeCH$_2$Me | —Me | —CHMeCH$_2$Me | —Me | —O—CMe$_3$ | 705 (M$^+$, 2); 632 (M$^+$ — OCMe$_3$, 7); 614 (26); 558 (39); 269 (100) |
| 21 | —H | —CH$_2$Ph | —Me | —CHMeCH$_2$Me | —Me | —CHMeCH$_2$Me | —Me | —OH | 573 (M$^+$, 2); 472 (15); 386 (36); 183 (85), 100 (60); 58 (100) |
| 22 | —H | —Me | —Me | —CHMeCH$_2$Me | —Me | —CHMeCH$_2$Me | —Me | —OH | 708 (M$^+$+ H, 2); 707 (M$^+$, 6); 148 (30); 91 (100) |
| 23 | —CO—O—CH$_2$Ph | —Me | —Me | —CHMeCH$_2$Me | —Me | —CHMeCH$_2$Me | —Me | —OH | 764 (M$^+$+ H, 4); 763 (M$^+$, 10); 419 (34); 386 (24); 183 (41); 91 (100) |
| 24 | —CO—O—CH$_2$Ph | —Me | —Me | —CHMeCH$_2$Me | —Me | —CHMeCH$_2$Me | —Me | —O—CMe$_3$ | 616 (M$^+$+ H, 2); 615 (M$^+$, 9); 386 (11); 183 (33); 100 (100) |
| 25 | —H | —(CH$_2$)$_3$—Me | —Me | —CHMeCH$_2$Me | —Me | —CHMeCH$_2$Me | —Me | —OH | |
| 26 | —CH$_2$Ph | —(CH$_2$)$_3$—Me | —Me | —CHMeCH$_2$Me | —Me | —CHMeCH$_2$Me | —Me | —OH | 761 (M$^+$, 1); 297 (10; 190 (100) |
| 27 | —CH$_2$Ph | —(CH$_2$)$_3$—Me | —Me | —CHMeCH$_2$Me | —Me | —CHMeCH$_2$Me | —Me | —O—CMe$_3$ | 651 (M$^+$+ H, 13); 650 (M$^+$, 38); 100 (100) |
| 28 | —H | —CHMeCH$_2$Me | —Me | —CH$_2$Ph | —Me | —CHMeCH$_2$Me | —Me | —OH | 740 (M$^+$+ H, 34); 190 (100) |
| 29 | —H | —CHMeCH$_2$Me | —Me | —CH$_2$Ph | —Me | —CHMeCH$_2$Me | —Me | —OH | 601 (M$^+$, 6); 472 (13); 486 (30); 183 (47); 86 (100) |
| 30 | —H | —(CH$_2$)$_2$—Me | —Me | —CHMeCH$_2$Me | —Me | —CHMeCH$_2$Me | —Me | —OH | 691 (M$^+$, 6); 572 (3); 176 (100) |
| 31 | —CH$_2$Ph | —(CH$_2$)$_2$—Me | —Me | —CHMeCH$_2$Me | —Me | —CHMeCH$_2$Me | —Me | —O—CMe$_3$ | 748 (M$^+$ + H, 2); 747 (M$^+$, 6); 628 (13); 176 (100 |
| 32 | —CH$_2$Ph | —(CH$_2$)$_2$—Me | —Me | —CHMeCH$_2$Me | —Me | —CHMeCH$_2$Me | —Me | —OH | 615 (M$^+$, 1); 472 (4); 183 (39); 100 (100) |
| 33 | —H | —(CH$_2$)$_2$—Me | —Me | —(CH$_2$)$_2$—Me | —Me | —CHMeCH$_2$Me | —Me | —OH | 705 (M$^+$, 6); 586 (16); 297 (15); 190 (100); 91 (37) |
| 34 | —CH$_2$Ph | —(CH$_2$)$_2$—Me | —Me | —(CH$_2$)$_2$—Me | —Me | —CHMeCH$_2$Me | —Me | —O—CMe$_3$ | 761 (M$^+$, 5); 586 (8); 297 (7); 190 (100) |
| 35 | —CH$_2$Ph | —(CH$_2$)$_3$—Me | —Me | —(CH$_2$)$_3$—Me | —Me | —CHMeCH$_2$Me | —Me | —OH | |
| 36 | —H | —CHMe$_2$ | —Me | —CHMeCH$_2$Me | —Me | —CHMeCH$_2$Me | —Me | —OH | 601 (M$^+$, 1); 386 (4); 176 (100) |
| 37 | —CH$_2$Ph | —CHMe$_2$ | —Me | —CHMeCH$_2$Me | —Me | —CHMeCH$_2$Me | —Me | —OH | 692 (M$^+$, 2); 648 (8); 176 (100) |

TABLE 1-continued

Examples of compounds of the formula (I; $R^7$ to $R^9$ = —Me)

| Ex. No. | A | $R^1$ | $R^2$ | $R^3$ | $R^4$ | $R^5$ | $R^6$ | B | Physical data[a] |
|---|---|---|---|---|---|---|---|---|---|
| 38 | —CH$_2$Ph | —CHMe$_2$ | —Me | —Me | —Me | —CHMeCH$_2$Me | —Me | —O—CMe$_3$ | 747 (M$^+$, 4); 674 (6); 628 (8); 176 (100) |
| 39 | —H | —(CH$_2$)$_2$—Me | —Me | —Me | —Me | —(CH$_2$)$_2$—Me | —Me | —OH | 574 (M$^+$ + H, 47); 299 (8); 186 (8); 96 (100) |
| 40 | —CH$_2$Ph | —(CH$_2$)$_2$—Me | —Me | —Me | —Me | —(CH$_2$)$_2$—Me | —Me | —OH | 663 (M$^+$, 6); 544 (21); 176 (100); 91 (36) |
| 41 | —CH$_2$Ph | —(CH$_2$)$_2$—Me | —Me | —Me | —Me | —(CH$_2$)$_2$—Me | —Me | —O—CMe$_3$ | 719 (M$^+$, 4); 544 (8); 176 (100) |
| 42 | —H | —CH$_2$CHMe$_2$ | —CH$_2$Ph | —CH$_2$Ph | —Me | —CH$_2$CHMe$_2$ | —Me | —OH | 914 (M$^+$, 2); 190 (100) |
| 43 | —CH$_2$Ph | —CH$_2$CHMe$_2$ | —CH$_2$Ph | —CH$_2$Ph | —Me | —CH$_2$CHMe$_2$ | —Me | —O—CMe$_3$ | 803 (M$^+$, 2); 684 (6); 339 (19); 190 (100) |
| 44 | —H | —CHMeCH$_2$Me | —(CH$_2$)$_3$—Me | —Me | —Me | —CHMeCH$_2$Me | —Me | —OH | 747 (M$^+$, 32); 690 (62); 628 (77); 419 (49); 310 (33); 181 (100) |
| 45 | —CH$_2$Ph | —CHMeCH$_2$Me | —(CH$_2$)$_3$—Me | —Me | —Me | —CHMeCH$_2$Me | —Me | —O—CMe$_3$ | 803 (M$^+$, 2); 684 (6); 339 (19); 190 (100) |
| 46 | —H | —CHMeCH$_2$Me | —(CH$_2$)$_3$—Me | —Me | —Me | —CHMeCH$_2$Me | —Me | —OH | 573 (M$^+$, 1); 358 (22); 176 (100) |
| 47 | —H | —CHMe$_2$ | —Me | —CHMe$_2$ | —Me | —CHMe$_2$ | —Me | —OH | 663 (M$^+$, 9); 620 (31); 176 (100) |
| 48 | —CH$_2$Ph | —CHMe$_2$ | —Me | —CHMe$_2$ | —Me | —CHMe$_2$ | —Me | —O—CMe$_3$ | 719 (M$^+$, 25); 544 (6); 269 (20); 176 (100) |
| 49 | —CH$_2$Ph | —CH$_2$Ph | —Me | —CH$_2$Ph | —Me | —CH$_2$Ph | —Me | —OH | 794 (M$^+$ + H, 14); 134 (100) |
| 50 | —H | —CH$_2$Ph | —Me | —CH$_2$Ph | —Me | —CH$_2$Ph | —Me | —O—CMe$_3$ | |
| 51 | —CH$_2$Ph | —CH$_2$Ph | —Me | —CH$_2$Ph | —Me | —CH$_2$Ph | —Me | —OH | 940 (M$^+$ + H, 17); 848 (5); 224 (100) |
| 52 | —H | —Me | —Me | —CH$_2$CHMe$_2$ | —CH$_2$Ph | —CH$_2$CHMe$_2$ | —Me | —O—CMe$_3$ | 573 (M$^+$, 19); 558 (16); 472 (18); 183 (71) |
| 53 | —H | —Me | —Me | —CHMeCH$_2$Me | —CH$_2$Ph | —CHMeCH$_2$Me | —Me | —OH | 707 (M$^+$, 8); 436 (8); 181 (18); 148 (44) |
| 54 | —CO—O—CH$_2$Ph | —Me | —Me | —CHMeCH$_2$Me | —CH$_2$Ph | —CHMeCH$_2$Me | —Me | —OH | 763 (M$^+$, 7); 707 (15); 651 (12); 91 (100) |
| 55 | —CO—O—CH$_2$Ph | —Me | —Me | —CH$_2$CHMe$_2$ | —CH$_2$Ph | —CH$_2$CHMe$_2$ | —Me | —O—CMe$_3$ | 768 (M$^+$ + H, 22); 403 (2); 100 (100) |
| 56 | —H | —CHMeCH$_2$Me | —Me | —CHMeCH$_2$Me | —CH$_2$Ph | —CHMeCH$_2$Me | —Me | —OH | 857 (M$^+$, 1); 800 (12); 738 (22); 190 (100) |
| 57 | —H | —CHMeCH$_2$Me | —Me | —CHMeCH$_2$Me | —CH$_2$Ph | —CHMeCH$_2$Me | —Me | —O—CMe$_3$ | 913 (M$^+$, 17); 794 (5); 373 (16) |
| 58 | —H | —CHMeCH$_2$Me | —Me | —CHMeCH$_2$Me | —Me | —CHMeCH$_2$Me | —Me | —O—CHMe$_3$ | 601 (M$^+$, 2); 544 (8); 386 (10); 255 (20) |
| 59 | —H | —CHMeCH$_2$Me | —H | —CHMeCH$_2$Me | —Me | —CHMeCH$_2$Me | —Me | —OH | 691 (M$^+$, 1); 634 (4); 572 (6) |
| 60 | —CH$_2$Ph | —CHMeCH$_2$Me | —H | —CHMeCH$_2$Me | —Me | —CHMeCH$_2$Me | —Me | —O—CMe$_3$ | 747 (M$^+$, 3); 690 (5); 190 (100 |
| 61 | —CH$_2$Ph | —H | —Me | —CHMeCH$_2$Me | —Me | —CHMeCH$_2$Me | —Me | —OH | 559 (M$^+$, 1); 358 (5); 271 (14); 100 (100) |
| 62 | —CH$_2$Ph | —H | —Me | —CHMeCH$_2$Me | —Me | —CHMeCH$_2$Me | —Me | —O—CMe$_3$ | 694 (M$^+$, 1); 405 (10); 91 (100) |
| 63 | —CO—O—CH$_2$Ph | —H | —Me | —CHMeCH$_2$Me | —Me | —CHMeCH$_2$Me | —Me | —OH | 749 (M$^+$, 10); 693 (18); 477 (24); 405 (34) |
| 64 | —CO—O—CH$_2$Ph | —H | —Me | —CHMeCH$_2$Me | —Me | —CHMeCH$_2$Me | —Me | —O—CMe$_3$ | 705 (M$^+$, 5); 586 (5); 190 (100) |
| 65 | —CH$_2$Ph | —CHMeCH$_2$Me | —Me | —CHMeCH$_2$Me | —Me | —CHMeCH$_2$Me | —Me | —OH | 761 (M$^+$, 1); 586 (5); 297 (10); 190 (100) |
| 66 | —CH$_2$Ph | —CHMeCH$_2$Me | —Me | —CHMeCH$_2$Me | —Me | —CHMeCH$_2$Me | —Me | —OH | 705 (M$^+$, 1); 586 (4); 190 (100) |
| 67 | —CH$_2$Ph | —CH$_2$CHMe$_2$ | —Me | —CH$_2$CHMe$_2$ | —Me | —CH$_2$CHMe$_2$ | —Me | —OH | 705 (M$^+$, 2); 646 (M$^+$ —OCMe$_3$, 2); 600 (5); 544 (6); 148 (100) |
| 68 | —CH$_2$Ph | —Me | —Me | —CHMeCH$_2$Me | —Me | —CHMeCH$_2$Me | —Me | —OH | 664 (M$^+$, 100); 528 (6); 148 (83) |
| 69 | —CH$_2$Ph | —Me | —Me | —CHMeCH$_2$Me | —Me | —Me | —Me | —OH | 489 (M$^+$, 1); 58 (100) |
| 70 | —H | —Me | —Me | —CHMeCH$_2$Me | —Me | —Me | —Me | —OH | 460 (M$^+$, 1); 119, 23) |
| 71 | —CH$_2$Ph | —Me | —Me | —CHMeCH$_2$Me | —Me | —Me | —Me | —OH | 635 (M$^+$, 2); 562 |
| 72 | —CH$_2$Ph | —Me | —Me | —CHMeCH$_2$Me | —Me | —Me | —Me | —O—CMe$_3$ | (M$^+$—OCMe$_3$, 4); 516 (3); 460 (3); 148 (100) |
| 73 | —H | —CHMeCH$_2$Me | —Me | —Me | —Me | —Me | —Me | —OH | 531 (M$^+$, 6); 487 (12); 474 (42); 388 (80) |
| 74 | —CH$_2$Ph | —CHMeCH$_2$Me | —Me | —Me | —Me | —Me | —Me | —OH | 621 (M$^+$, 2); 564 (2); 502 (3); 335 (5); 190 (100) |
| 75 | —CH$_2$Ph | —CHMeCH$_2$Me | —Me | —Me | —Me | —Me | —Me | —O—CMe$_3$ | 677 (M$^+$, 2); 620 |

TABLE 1-continued

Examples of compounds of the formula (I; $R^7$ to $R^9$ = —Me)

| Ex. No. | A | $R^1$ | $R^2$ | $R^3$ | $R^4$ | $R^5$ | $R^6$ | B | Physical data[a] |
|---|---|---|---|---|---|---|---|---|---|
| 76 | —H | —CH$_2$CHMe$_2$ | —Me | —CHMeCH$_2$Me | —Me | —Me | —Me | —OH | (M$^+$ — OCMe$_3$; 5); 558 (2); 502 (2); 190 (100) |
| 77 | —CO—O—CH$_2$Ph | —CH$_2$CHMe$_2$ | —Me | —CHMeCH$_2$Me | —Me | —Me | —Me | —OH | 573 (M$^+$, 1); 430 (3); 100 (100) |
| 78 | —CO—O—CH$_2$Ph | —CH$_2$CHMe$_2$ | —Me | —CHMeCH$_2$Me | —Me | —Me | —Me | —O—CMe$_3$ | 707 (M$^+$, 1); 607 (1); 461 (3); 190 (59); 91 (100) |
| 79 | —H | —Me | —Me | —CHMe$_2$ | —Me | —CHMe$_2$ | —Me | —OH | 763 (M$^+$, 2); 707 (9); 651 (7); 533 (9); 91 (100) |
| 80 | —CH$_2$Ph | —Me | —Me | —CHMe$_2$ | —Me | —CHMe$_2$ | —Me | —OH | 545 (M$^+$, 2); 501 (81); 358 (27); 169 (80); 53 (100) |
| 81 | —CH$_2$Ph | —Me | —Me | —CHMe$_2$ | —Me | —CHMe$_2$ | —Me | —O—CMe$_3$ | 635 (M$^+$, 1); 516 (4); &1 (2); 143 (100) |
| 82 | —H | —(CH$_2$)$_2$—Me | —Me | —Me | —Me | —CHMeCH$_2$Me | —Me | —OH | 691 (M$^+$, 1); 618 (2); 572 (3); 516 (3); 148 (100) |
| 83 | —CH$_2$Ph | —(CH$_2$)$_2$—Me | —Me | —Me | —Me | —CHMeCH$_2$Me | —Me | —OH | 559 (M$^+$, 1); 86 (100) |
| 84 | —CH$_2$Ph | —(CH$_2$)$_2$—Me | —Me | —Me | —Me | —CHMeCH$_2$Me | —Me | —O—CMe$_3$ | 649 (M$^+$, 1); 530 (4); 176 (100) |
| 85 | —H | —CHMe$_2$ | —Me | —Me | —Me | —CHMeCH$_2$Me | —Me | —OH | 705 (M$^+$, 2); 632 |
| 86 | —CH$_2$Ph | —CHMe$_2$ | —Me | —Me | —Me | —CHMeCH$_2$Me | —Me | —OH | (M$^+$ — OCMe$_3$; 2); 586 (3); 530 (3); 176 (100) |
| 87 | —CH$_2$Ph | —CHMe$_2$ | —Me | —Me | —Me | —CHMeCH$_2$Me | —Me | —O—CMe$_3$ | 649 (M$^+$, 2); 606 (4); 530 (8); 176 (100) |
| 88 | —H | —H | —Me | —Me | —Me | —CHMeCH$_2$Me | —Me | —OH | 705 (M$^+$, 2); 632 (M$^+$ — OCMe$_3$, 3); 586 (5); 530 (7); 176 (100) |
| 89 | —CO—O—CH$_2$Ph | —H | —Me | —Me | —Me | —CHMeCH$_2$Me | —Me | —OH | 652 (M$^+$ + H, 24); 608 (3); 363 (24); 91 (100) |
| 90 | —CO—O—CH$_2$Ph | —H | —Me | —Me | —Me | —CHMeCH$_2$Me | —Me | —O—CMe$_3$ | 707 (M$^+$, 7); 650 (M$^+$ — CMe$_3$, 15); 435 (15); 91 (100) |
| 91 | —H | —CH$_2$CHMe$_2$ | —Me | —Me | —Me | —Me | —Me | —OH | 707 (M$^+$, 1); 651 (2); 419 (5); 91 (100) |
| 92 | —CO—O—CH$_2$Ph | —CH$_2$CH—Me$_2$ | —Me | —Me | —Me | —Me | —Me | —OH | 763 (M$^+$, 2); 190 (48); 91 (100) |
| 93 | —CO—O—CH$_2$Ph | —CH$_2$CHMe$_2$ | —Me | —Me | —Me | —Me | —Me | —O—CMe$_3$ | 531 (M$^+$, 3); 487 (4); 388 (19); 100 (100) |
| 94 | —H | —CH$_2$CHMe$_2$ | —Me | —Me | —Me | —Me | —Me | —OH | 621 (M$^+$, 0.5); 190 (100) |
| 95 | —CH$_2$Ph | —CH$_2$CHMe$_2$ | —Me | —Me | —Me | —Me | —Me | —OH | 677 (M$^+$, 2); 604 (4); 190 (100) |
| 96 | —CH$_2$Ph | —CH$_2$CHMe$_2$ | —Me | —Me | —Me | —Me | —Me | —O—CMe$_3$ | 607 (M$^+$, 0.5); 550 (3); 464 (8); 361 (3); 100 (100) |
| 97 | —CH$_2$Ph | —CHMeCH$_2$Me | —CH$_2$Ph | —Me | —Me | —Me | —Me | —OH | 697 (M$^+$, 0.5); 190 (100) |
| 98 | —CH$_2$Ph | —CHMeCH$_2$Me | —CH$_2$Ph | —Me | —Me | —Me | —Me | —OH | 753 (M$^+$, 1); 696 (2); 634 (3); 578 (2); 190 (100) |
| 99 | —CH$_2$Ph | —CHMeCH$_2$Me | —CH$_2$Ph | —Me | —Me | —Me | —Me | —O—CMe$_3$ | 559 (M$^+$, 0.5); 502 (8); 416 (12); 255 (21); 100 (100) |
| 100 | —CH$_2$Ph | —CHMeCH$_2$Me | —CHMe$_2$ | —Me | —Me | —Me | —Me | —OH | 649 (M$^+$, 0.5); 190 (100) |
| 101 | —CH$_2$Ph | —CHMeCH$_2$Me | —CHMe$_2$ | —Me | —Me | —Me | —Me | —OH | 705 (M$^+$, 3); 530 (2); 501 (2); 190 (100) |
| 102 | —CH$_2$Ph | —CHMeCH$_2$Me | —CHMe$_2$ | —Me | —Me | —Me | —Me | —O—CMe$_3$ | 517 (M$^+$, 0.5); 474 (4); 227 (21); 141 (29); 86 (100) |
| 103 | —H | —CHMe$_2$ | —Me | —Me | —Me | —Me | —Me | —OH | 607 (M$^+$, 0.5); 176 (100) |
| 104 | —CH$_2$Ph | —CHMe$_2$ | —Me | —Me | —Me | —Me | —Me | —OH | 663 (M$^+$, 2); 620 (4); 590 (6); 544 (6); 176 (100) |
| 105 | —CH$_2$Ph | —CHMe$_2$ | —Me | —Me | —Me | —Me | —Me | —O—CMe$_3$ | 649 (M$^+$, 0.5); 592 (3); 506 (6) 100 (100) |
| 106 | —H | —CHMeCH$_2$Me | —CH$_2$Ph | —Me | —CHMeCH$_2$Me | —Me | —Me | —OH | 739 (M$^+$, 0.5); 620 (2); 453 (3); 190 (100) |
| 107 | —CH$_2$Ph | —CHMeCH$_2$Me | —CH$_2$Ph | —Me | —CHMeCH$_2$Me | —Me | —Me | —OH | 795 (M$^+$, 1); 738 (3); 676 (3); 620 (2); 190 (100) |
| 108 | —CH$_2$Ph | —CHMeCH$_2$Me | —CH$_2$Ph | —Me | —CHMeCH$_2$Me | —Me | —Me | —O—CMe$_3$ | 601 (M$^+$, 0.5); 544 (4); 458 (5); 100 (100) |
| 109 | —H | —CHMeCH$_2$Me | —CHMe$_2$ | —Me | —CHMeCH$_2$Me | —Me | —Me | —OH | 691 (M$^+$, 1); 634 (3); 572 (8); 325 (8); 190 (100) |
| 110 | —CH$_2$Ph | —CHMeCH$_2$Me | —CHMe$_2$ | —Me | —CHMeCH$_2$Me | —Me | —Me | —OH | 747 (M$^+$, 1); 628 (6); 572 (7); 190 (100) |
| 111 | —CH$_2$Ph | —CHMeCH$_2$Me | —CHMe$_2$ | —Me | —CHMeCH$_2$Me | —Me | —Me | —O—CMe$_3$ | 559 (M$^+$, 1); 503 (2); 58 (100) |
| 112 | —H | —Me | —H | —CHMeCH$_2$Me | —Me | —CHMeCH$_2$Me | —Me | —OH | |

TABLE 1-continued

Examples of compounds of the formula (I; $R^7$ to $R^9$ = —Me)

| Ex. No. | A | $R^1$ | $R^2$ | $R^3$ | $R^4$ | $R^5$ | $R^6$ | B | Physical data[a] |
|---|---|---|---|---|---|---|---|---|---|
| 113 | —CH₂Ph | —Me | —H | —CHMeCH₂Me | —Me | —CHMeCH₂Me | —Me | —OH | 649 (M⁺, 1); 148 (100) |
| 114 | —CH₂Ph | —Me | —H | —CHMeCH₂Me | —Me | —CHMeCH₂Me | —Me | —O—CMe₃ | 705 (M⁺, 2); 632 (4); 586 (5); 148 (100) |
| 115 | —H | —CHMeCH₂Me | —CHMe₂ | —CHMeCH₂Me | —Me | —Me | —CHMe₂ | —OH | 629 (M⁺, 0.5); 572 (7); 486 (7) 100 (100) |
| 116 | —CH₂Ph | —CHMeCH₂Me | —CHMe₂ | —CHMeCH₂Me | —Me | —Me | —CHMe₂ | —OH | 719 (M⁺, 1); 662 (2); 600 (3); 325 (3); 190 (100) |
| 117 | —CH₂Ph | —CHMeCH₂Me | —CHMe₂ | —CHMeCH₂Me | —Me | —Me | —CHMe₂ | —O—CMe₃ | 775 (M⁺, 2); 656 (5); 600 (8); 190 (100) |
| 118 | —CO—O—CMe₃ | —CHMeCH₂Me | —Me | —Me | —Me | —CHMeCH₂Me | —Me | —OH | 573 (M⁺, 1); 516 (10); 100 (100) |
| 119 | —CO—O—CMe₃ | —CHMeCH₂Me | —Me | —Me | —Me | —CHMeCH₂Me | —Me | —O—CMe₃ | 729 (M⁺, 1); 673 (1); 572 (18); 430 (20); 144 (100) |
| 120 | —H | —CH₂Me | —Me | —CHMeCH₂Me | —Me | —CHMeCH₂Me | —Me | —OH | 563 (M⁺, 1); 472 (14); 386 (28); 72 (100) |
| 121 | —CO—O—CH₂Ph | —CH₂Me | —Me | —CHMeCH₂Me | —Me | —CHMeCH₂Me | —Me | —OH | 721 (M⁺, 2); 91 (100) |
| 122 | —CO—O—CH₂Ph | —CH₂Me | —Me | —CHMeCH₂Me | —Me | —CHMeCH₂Me | —Me | —O—CMe₃ | 777 (M⁺, 8); 721 (15); 505 (20); 91 (100) |
| 123 | —H | —CH₂Me | —Me | —Me | —Me | —CHMeCH₂Me | —Me | —OH | 547 (M⁺ + H 2); 546 (M⁺, 12); 512 (13) |
| 124 | —CO—O—CH₂Ph | —CH₂Me | —Me | —Me | —Me | —CHMeCH₂Me | —Me | —OH | 679 (M⁺, 8); 544 (3); 430 (9); 91 (100) |
| 125 | —CO—O—CH₂Ph | —CH₂Me | —Me | —Me | —Me | —CHMeCH₂Me | —Me | —O—CMe₃ | 735 (M⁺, 13); 679 (30); 463 (36); 91 (100) |
| 126 | —H | —CHMeCH₂Me | —H | —Me | —Me | —CHMeCH₂Me | —Me | —OH | 599 (M⁺, 2); 213 (28); 100 (100) |
| 127 | —CH₂Ph | —CHMeCH₂Me | —H | —Me | Me | —CHMeCH₂Me | —Me | —OH | 430 (M⁺, 3); 357 (19); 329 (19); 273 (35); 58 (100) |
| 128 | —CH₂Ph | —CHMeCH₂Me | —H | —Me | —Me | —CHMeCH₂Me | —Me | —O—CMe₃ | 705 (M⁺, 0.5); 648 (6); 530 (5); 190 (100) |
| 129 | —CO—O—CH₂Ph | —CO—O—CH₂Ph | —Me | —CHMeCH₂Me | —Me | —CHMeCH₂Me | —Me | —O—CMe₃ | 869 (M⁺, 4); 704 (10); 91 (100) |
| 130 | —CO—O—CH₂Ph | —CO—O—CH₂Ph | —Me | —CHMeCH₂Me | —Me | —CHMeCH₂Me | —Me | —OH | 814 (M⁺, 3); 680 (14); 597 (4); 525 (33), 91 (100) |

[a]FAB - MS bzw. EI-MS m/z (%)

Me = Methyl
Ph = Phenyl

Starting substances of the formula (II) and (III)

EXAMPLE (II-1)

tert-Butyl N-benzyl-N-methyl-L-leucyl-D-lactyl-N-methyl-L-leucyl-D-lactate

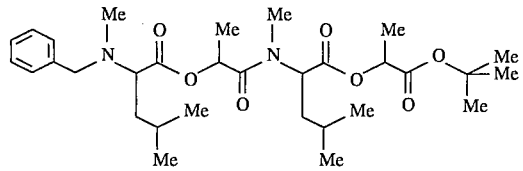

The coupling reaction is carried out analogously to the reaction protocol of Example 1, but 12.4 g (40.3 mmol) of N-benzyl-N-methyl-L-leucyl-D-lactic acid, 11.0 g (40.3 mmol) of tert-butyl N-methyl-L-leucyl-D-lactate, 100 ml of methylene chloride, 11.5 g (88.7 mmol) of N,N-diisopropylethylamine "Hünig base"), 11.3 g (44.3 mmol) of bis(2-oxo-3-oxazolidihyl)-phosphinic chloride (BOP-Cl)

are used.

The crude product which remains is chromatographed over a silica gel column (silica gel 60—Merck, mesh size: 0.04 to 0.063 mm) using toluene: ethyl acetate (20:1) as the eluent. 21.8 g (96.0% of theory) of tert-butyl N-benzyl-N-methyl-L-leucyl-D-lactyl-N-methyl-L-leucyl-D-lactate are obtained.

EI-MS m/z (%): 562 (M$^+$, 3); 489 (M$^+$—OCMe$_3$, 7); 443 (2); 387 (3); 344 (1); 190 (PhCH$_2$—NMe—CH—CH$_2$Me$_2$, 100); 120 (PhCH$_2$—NMe—, 31)

EXAMPLE (II-2)

N-Benzyl-N-methyl-L-isoleucyl-D-lactyl-N-methyl-L-isoleucyl-D-lactic acid

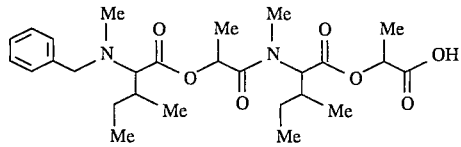

C-Terminal acidolysis is carried out analogous to the reaction protocol of Example 3, but 9.0 g (16.0 mmol) of tert-butyl N-benzyl-N-methyl-L-isoleucyl-D-lactyl-N-methyl-L-isoleucyl-D-lactate and 300 ml of methylene chloride are used.

8.2 g (100% of theory) of N-benzyl-N-methyl-L-isoleucyl-D-lactyl-N-methyl-L-isoleucyl-D-lactic acid are obtained.

EI-MS m/z (%): 506 (M$^+$, 3); 449 (7); 190 (PhCH$_2$—NMe—CH—CHMeCH$_2$Me, 100)

EXAMPLE (III-1)

tert-Butyl N-methyl-L-leucyl-D-lactyl-N-methyl-L-leucyl-D-lactate

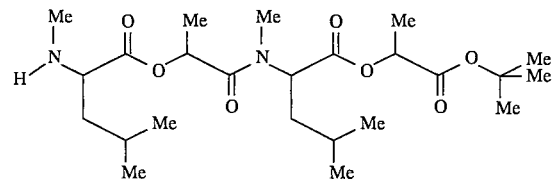

21.8 g (38.7 mmol) of Bn-(-L-MeLeu-D-Lac-)$_2$—O—$^t$Bu are dissolved in 300 ml of ethanol and hydrogenated in the presence of 2.2 g of Pd(OH)$_2$/charcoal [Pd content: 20%] until hydrogen is no longer taken up (approximately 2.5 hours). After the catalyst has been filtered off, the entire reaction solution is concentrated in vacuo. 18.3 g (100% of theory) of tert-butyl N-methyl-L-leucyl-D-lactyl-N-methyl-L-leucyl-D-lactate are obtained, and this can be used for the coupling reaction without further purification.

EI-MS m/z (%): 472 (M$^+$,4); 457 (1); 428 (1); 399 (6); 100 (HNMe—CH—CH$_2$Me$_2$,100)

The compounds of the general formula (III; R$^8$, R$^9$=Me) listed in Table 2 below can be prepared analogously in the form of the LDLD stereoisomers.

TABLE 2

Examples of compounds of the formula (III; R$^8$, R$^9$ = —Me)

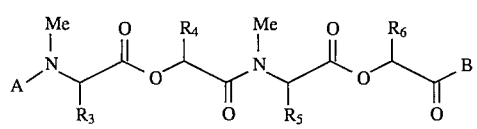

| Ex. No. | A | R$^3$ | R$^4$ | R$^5$ | R$^6$ | B | Physical data[a] |
|---|---|---|---|---|---|---|---|
| III-2 | —CH$_2$Ph | —CH$_2$CHMe$_2$ | —CH$_2$Ph | —CH$_2$CHMe$_2$ | —Me | —O—CMe$_3$ | |
| III-3 | —H | —CH$_2$CHMe$_2$ | —CH$_2$Ph | —CH$_2$CHMe$_2$ | —Me | —O—CMe$_3$ | |
| III-4 | —CH$_2$Ph | —CHMeCH$_2$Me | —CHMe$_2$ | —CH$_2$Ph | —CHMe$_2$ | —O—CMe$_3$ | 652 (M$^+$, 8); 595 (M$^+$—CMe$_3$, 14); 579 (M$^+$—OCMe$_3$, 16); 533 (12); 477 (24); 190 (100) |

TABLE 2-continued

Examples of compounds of the formula (III; $R^8$, $R^9$ = —Me)

$$A-\underset{R_3}{\underset{|}{N}}(Me)-\underset{}{C}(=O)-O-\underset{R_4}{\underset{|}{CH}}-C(=O)-\underset{R_5}{\underset{|}{N}}(Me)-C(=O)-O-\underset{R_6}{\underset{|}{CH}}-C(=O)-B$$

| Ex. No. | A | $R^3$ | $R^4$ | $R^5$ | $R^6$ | B | Physical data[a] |
|---|---|---|---|---|---|---|---|
| III-5 | —H | —CHMeCH$_2$Me | —CHMe$_2$ | —CH$_2$Ph | —CHMe$_2$ | —O—CMe$_3$ | 562 (M$^+$, 2); 518 (2); 489 (M$^+$ — OCMe$_3$, 4); 363 (7); 100 (100) |
| III-6 | —CH$_2$Ph | —CHMeCH$_2$Me | —Me | —CHMeCH$_2$Me | —Me | —O—CMe$_3$ | 563 (M$^+$ + 11, 1); 562 (M$^+$, 3); 505 (M$^+$ — CMe$_3$, 7); 489 (M$^+$ — OCMe$_3$, 6); 190 (100) |
| III-7 | —H | —CHMeCH$_2$Me | —Me | —CHMeCH$_2$Me | —Me | —O—CMe$_3$ | 472 (M$^+$, 1); 359 (11); 273 (6); 100 (100) |
| III-8 | —CH$_2$Ph | —(CH$_2$)$_3$—Me | —Me | —(CH$_2$)$_3$—Me | —Me | —O—CMe$_3$ | 563 (M$^+$ + H, 1); 562 (M$^+$, 3); 489 (5); 190 (100) |
| III-9 | —CH$_2$Ph | —CHMe$_2$ | —Me | —CHMe$_2$ | —Me | —O—CMe$_3$ | 534 (M$^+$, 6); 491 (7); 461 (10); 176 (100) |
| III-10 | —CH$_2$Ph | —(CH$_2$)$_2$—Me | —Me | —(CH$_2$)$_2$—Me | —Me | —O—CMe$_3$ | 534 (M$^+$, 2); 461 (6); 176 (100) |
| III-11 | —CH$_2$Ph | —CHMe$_2$ | —Me | —CHMe$_2$ | —Me | —O—CMe$_3$ | 534 (M$^+$, 6); 491 (7); 461 (10); 176 (100) |
| III-12 | —CH$_2$Ph | —CHMeCH$_2$Me | —CH$_2$Ph | —CHMeCH$_2$Me | —Me | —O—CMe$_3$ | 638 (M$^+$, 5); 565 (M$^+$ — OCMe$_3$, 5); 463 (5); 190 (100) |
| III-13 | —H | —CHMeCH$_2$Me | —CH$_2$Ph | —CHMeCH$_2$Me | —Me | —O—CMe$_3$ | 548 (M$^+$, 1); 475 (M$^+$ — OCMe$_3$, 5); 349 (5); 100 (100) |
| III-14 | —CH$_2$Ph | —CH$_2$Ph | —CH$_2$Ph | —CH$_2$Ph | —Me | —O—CMe$_3$ | 707 (M$^+$ + H, 5); 706 (M$^+$, 9); 633 (M$^+$ — OCMe$_3$, 7); 615 (46); 224 (94); 91 (100) |
| III-15 | —H | —CH$_2$Ph | —CH$_2$Ph | —CH$_2$Ph | —Me | —O—CMe$_3$ | 616 (M$^+$, 2); 601 (M$^+$ — Me, 2); 543 (M$^+$ — O — CMe$_3$, 4); 525 (29); 469 (70); 134 (100) |
| III-16 | —CH$_2$Ph | —Me | —Me | —Me | —Me | —O—CMe$_3$ | 478 (M$^+$, 1); 405 (M$^+$ — OCMe$_3$, 6); 148 (100) |
| III-17 | —H | —Me | —Me | —Me | —Me | —O—CMe$_3$ | 388 (M$^+$, 0.5); 344 (M$^+$ — CO$_2$, 4); 315 (15); 58 (100) |
| III-18 | —CH$_2$Ph | —CHMeCH$_2$Me | —Me | —Me | —Me | —O—CMe$_3$ | 520 (M$^+$, 2); 463 (M$^+$ — CMe$_3$, 6); 447 (M$^+$ — OCMe$_3$, 8), 190 (100) |
| III-19 | —H | —CHMeCH$_2$Me | —Me | —Me | —Me | —O—CMe$_3$ | 432 (M$^+$ + H, 3); 431 (M$^+$, 12), 190 (100) |
| III-20 | —H | —CHMe$_2$ | —Me | —CHMe$_2$ | —Me | —O—CMe$_3$ | 444 (M$^+$, 0.5); 400 (2); 371 (6): 345 (9); 86 (100) |
| III-21 | —CH$_2$Ph | —Me | —Me | —CHMeCH$_2$Me | —Me | —O—CMe$_3$ | 520 (M$^+$, 2); 447 (6); 345 (2); 148 (100) |
| III-22 | —H | —Me | —Me | —CHMeCH$_2$Me | —Me | —O—CMe$_3$ | 432 (M$^+$ + H, 100); 375 (39); 274 (26); 218 (24); 100 (34) |

[a]FAB-MS or EI-MS m/z (%)

Starting substances of the forzula (IV), (V) and (VI)

EXAMPLE (IV-1)

tert-Butyl N-benzyloxycarbonyl-N-methyl-L-leucyl-D-lactate

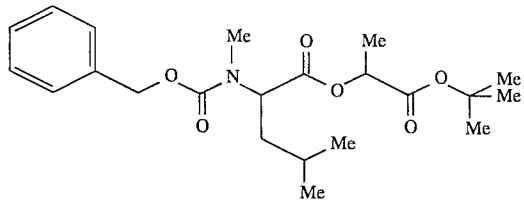

10.0 g (35.8 mmol) of N-benzyloxycarbonyl-N-methyl-L-leucine are dissolved in 150 ml of methanol and 15 ml of water, 19.5 ml of a 20% strength caesium carbonate solution are added, and the mixture is stirred at room temperature for approximately one hour. Two portions of approximately 50 ml of absolute dimethylformamide are subsequently added, the mixture is concentrated in vacuo, and the product is dried under a high vacuum. The caesium salt is introduced into 75 ml of dimethylforma,mide, 7.0 g (35.8 mmol) of tert-butyl L-2-chloro-propionic acid are added, and the mixture is stirred for approximately 18 hours at room temperature. The entire reaction solution is concentrated in vacuo, the oily residue is taken up in methylene chloride, and the mixture is shaken twice with water. The organic phase is then separated off, dried over sodium sulphate and concentrated in vacuo. The crude product which remains is chromatographed over a silica gel column (silica gel 60—Merck, mesh size: 0.04 to 0.063 MM) using toluene: ethyl acetate (40: 1) as the eluent.

14.4 g (100% of theory) of tert-butyl N-benzyloxycarbonyl-N-methyl-L-leucyl-D-lactate are obtained.

EI-MS m/z (%): 407 (M$^+$,2); 351 (10); 234 (39); 387 (3); 344 (1); 190 (PhCH$_2$—NMe—CH—CH$_2$Me$_2$,69); 91 (PhCH$_2$,100)

EXAMPLE (V -1)

N-Benzyl-N-methyl-L-isoleucyl-D-hydroxyisovaleric acid

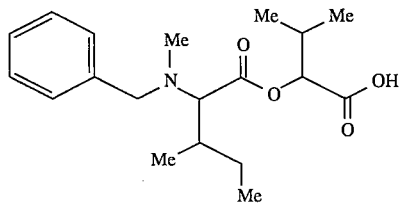

C-Terminal acidolysis is carried out analogously to the reaction protocol of Example (I-2), but 10.5 g (26.8 mmol) of tert-butyl N-benzyl-N-methyl-L-isoleucyl-D-hydroxyisovalerate 250 ml of methylene chloride are used.

8.5 g (94.5% of theory) of N-benzyl-N-methyl-L-isoleucyl-D-hydroxyisovaleric acid are obtained, and this can be reacted further without further purification.

EI-MS: m/z (%): 335 (M$^+$,1); 278 (19); 190 (PhCH$_2$—NMe—CH—CHMeCH$_2$Me,100); 91 (PhCH$_2$,84)

EXAMPLE VI -1)

tert-Butyl N-methyl-L-phenylalanyl-D-hydoxyvalerate

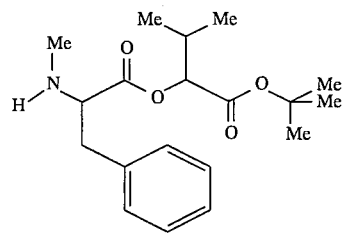

N-Terminal deblocking is carried out analogously to the reaction protocol of Example (III-2), but 10.0 g (23.5 mmol) of tert-butyl N-benzyl-N-methyl-L-phenylalanyl -D -hydroxyisovalerate, 250 ml of ethanol and 1.0 g of Pd (OH)$_2$/charcoal [Pd content: 20%]

are used.

7.5 g (95.2% of theory) of tert-butyl N-methyl-L-phenylalanyl-D-hydroxyvalerate are obtained, and this can be reacted further without further purification.

$^1$H-NMR (400 MHz, CDCl$_3$, δ): 0.80; 0.85 (2d, 6H, 2×—CH$_3$; J=6.9 Hz); 1.46 (s, 9H, —C(CH$_3$)$_3$); 2.42 (s, 3H, —N—CH$_3$); 2.94; 2.97 (2d, 2H, —CH$_2$—Phe); 3.55 (m, 1H,—O—CH); 4.58 (d, 1H, —N—CH; J=4.7 Hz); 7.18–7.26 (m, 5H, aromatic H) ppm EI-MS m/z (%): 336 (M$^+$+H, 7); 335 (M$^+$,2); 262 (M$^+$—O—CMe$_3$,12); 188 (100); 134 (81)

The compounds of the general formulae (IV; R$^7$=Me ), V; R$^8$ =—Me) and (VI; R$^9$=—Me) listed in Tables 3, 4 and 5 below can be prepared analogously in the form of the L-D stereoisomers.

TABLE 3

Examples of compounds of the general formula (IV); R$^7$ = —Me)

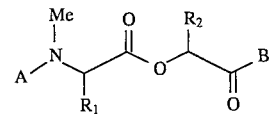

| Ex. No. | A | R$^1$ | R$^2$ | B | Physical data$^{a)}$ |
|---|---|---|---|---|---|
| IV-2 | —CO—O—CH$_2$—Ph | —CHMeCH$_2$Me | —CHMe$_2$ | —O—CMe$_3$ | |
| IV-3 | —CO—O—CH$_2$—Ph | —CHMeCH$_2$Me | —CHMe$_2$ | —OH | |
| IV-4 | —CO—O—CH$_2$—Ph | —CHMeCH$_2$Me | —Me | —O—CMe$_3$ | 407 (M$^+$, 7) |
| IV-5 | —CO—O—CH$_2$—Ph | —CHMeCH$_2$Me | —Me | —OH | |
| IV-6 | —CH$_2$Ph | —CH$_2$CHMe$_2$ | —Me | —O—CMe$_3$ | 363 (M$^+$, 1) |
| IV-7 | —CH$_2$Ph | —CH$_2$CHMe$_2$ | —Me | —OH | 307 (M$^+$, 7) |
| IV-8 | —CH$_2$Ph | —CH$_2$PHe | —Me | —O—CMe$_3$ | 397 (M$^+$, 2) |
| IV-9 | —CH$_2$Ph | —CH$_2$PHe | —Me | —OH | |
| IV-10 | —CH$_2$Ph | —CH$_2$CHMe$_2$ | —CHMe$_2$ | —O—CMe$_3$ | 391 (M$^+$, 1) |
| IV-11 | —CH$_2$Ph | —CH$_2$CHMe$_2$ | —(CH$_2$)$_3$—Me | —O—CMe$_3$ | 405 (M$^+$, 5) |
| IV-12 | —CH$_2$Ph | —CH$_2$CHMe$_2$ | —(CH$_2$)$_2$—Me | —OH | 349 (M$^+$, 14) |
| IV-13 | —CH$_2$Ph | —CHMeCH$_2$Me | —(CH$_2$)$_3$—Me | —O—CMe$_3$ | 405 (M$^+$, 2) |
| IV-14 | —CH$_2$Ph | —CHMeCH$_2$Me | —(CH$_2$)$_2$—Me | —OH | 350 (M$^+$, 100) |
| IV-15 | —CH$_2$Ph | —CHMeCH$_2$Me | —CH$_2$—Ph | —O—CMe$_3$ | 439 (M$^+$, 3) |
| IV-16 | —CH$_2$Ph | —CHMe$_2$ | —Me | —OH | 293 (M$^+$, 4) |
| IV-17 | —CH$_2$Ph | —(CH$_2$)$_3$Me | —Me | —OH | 307 (M$^+$, 1) |
| IV-18 | —CO—O—CH$_2$—Ph | —Me | —Me | —O—CMe$_3$ | 309 (16)$^{b)}$ |
| IV-19 | —CO—O—CH$_2$—Ph | —H | —Me | —O—CMe$_3$ | 295 (22)$^{b)}$ |
| IV-20 | —CO—O—CH$_2$—Ph | —H | —Me | —OH | 295 (M$^+$, 10) |
| IV-21 | —CH$_2$Ph | —CHMeCH$_2$Me | —H | —O—CMe$_3$ | 349 (M$^+$, 3) |
| IV-22 | —CH$_2$Ph | —CHMeCH$_2$Me | —H | —OH | 239 (M$^+$, 3) |

TABLE 4

Examples of compounds of the general formula (V; $R^8 = -Me$)

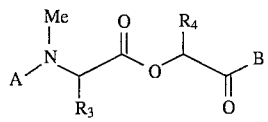

| Ex. No. | A | $R^3$ | $R^4$ | B | Physical data[a] |
|---|---|---|---|---|---|
| V-2 | $-CH_2-Ph$ | $-CH_2CHMe_2$ | $-CH_2-Ph$ | $-O-CMe_3$ | 1.44 ($-C\underline{Me}_3$); 2.21 ($-N-\underline{Me}$) |
| V-3 | $-CH_2-Ph$ | $-CH_2CHMe_2$ | $-CH_2-Ph$ | $-OH$ | |
| V-4 | $-CH_2-Ph$ | $-CHMeCH_2Me$ | $-CHMe_2$ | $-O-CMe_3$ | 1.50 ($-C\underline{Me}_3$); 2.28 ($-N-\underline{Me}$) |
| V-5 | $-CH_2-Ph$ | $-CHMeCH_2Me$ | $-Me$ | $-O-CMe_3$ | 1.49 ($-C\underline{Me}_3$); 2.26 ($-N-\underline{Me}$) |
| V-6 | $-CH_2-Ph$ | $-CHMeCH_2Me$ | $-Me$ | $-OH$ | |
| V-7 | $-CH_2-Ph$ | $-(CH_2)_2Me$ | $-Me$ | $-O-CMe_3$ | 1.49 ($-C\underline{Me}_3$); 2.32 ($-N-\underline{Me}$) |
| V-8 | $-CH_2-Ph$ | $-(CH_2)_2Me$ | $-Me$ | $-OH$ | 239 ($M^+$, 1); 176 (100) |
| V-9 | $-CH_2-Ph$ | $-CHMe_2$ | $-Me$ | $-O-CMe_3$ | 250 ($M^+$, 7); 250 (10) |
| V-10 | $-CH_2-Ph$ | $-(CH_2)_3Me$ | $-Me$ | $-O-CMe_3$ | 1.49 ($-C\underline{Me}_3$); 232 ($-N-\underline{Me}$) |
| V-11 | $-CH_2-Ph$ | $-CH_2CHMe_2$ | $-Me$ | $-O-CMe_3$ | 1.49 ($-C\underline{Me}_3$); 2.33 ($-N-\underline{Me}$) |
| V-12 | $-CH_2-Ph$ | $-CHMeCH_2Me$ | $-CH_2-Ph$ | $-OH$ | |
| V-13 | $-CH_2-Ph$ | $-Me$ | $-Me$ | $-OH$ | 265 ($M^+$, 2); 148 (100) |
| V-14 | $-CH_2-Ph$ | $-CH_2-Ph$ | $-CH_2-Ph$ | $-OH$ | 417 ($M^+$, 3); 326 (57) |

[a] $^1$H-NMR (400 MHz, CDCl$_3$, δ) in ppm; in each case singlets; FAB- or EI-MS m/z (%)

TABLE 5

Examples of compounds of the general formula (VI; $R^9 = -Me$)

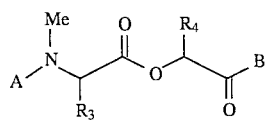

| Ex. No. | A | $R^5$ | $R^6$ | B | Physical data[a] |
|---|---|---|---|---|---|
| VI-2 | $-CH_2-Ph$ | $-CH_2-Ph$ | $-CHMe_2$ | $-O-CMe_3$ | 1.49 ($-C\underline{Me}_3$); 2,41 ($-N-\underline{Me}$) |
| VI-3 | $-H$ | $-CH_2-Ph$ | $-Me$ | $-O-CMe_3$ | 1.48 ($-C\underline{Me}_3$); 2.40 ($-N-Me$) |
| VI-4 | $-H$ | $-CHMeCH_2Me$ | $-Me$ | $-O-CMe_3$ | |
| VI-5 | $-H$ | $-CHMe_2$ | $-Me$ | $-O-CMe_3$ | 1.47 ($-C\underline{Me}_3$); 2.40 ($-N-\underline{Me}$) |
| VI-6 | $-H$ | $-(CH_2)_2-Me$ | $-Me$ | $-O-CMe_3$ | 1.47 ($-C\underline{Me}_3$); 2.44 ($-N-\underline{Me}$) |
| VI-7 | $-H$ | $-CH_2CHMe_2$ | $-Me$ | $-O-CMe_3$ | 1.47 ($-C\underline{Me}_3$); 2.53 ($-N-\underline{Me}$) |
| VI-8 | $-H$ | $-CH_2-Ph$ | $-Me$ | $-O-CMe_3$ | 1.45 ($-C\underline{Me}_3$); 2.42 ($-N-\underline{Me}$) |
| VI-9 | $-H$ | $-(CH_2)_3-Me$ | $-Me$ | $-O-CMe_3$ | 1.47 ($-C\underline{Me}_3$); 2.41 ($-N-\underline{Me}$) |
| VI-10 | $-CH_2-Ph$ | $-Me$ | $-Me$ | $-O-CMe_3$ | 1.47 ($-C\underline{Me}_3$); 2.34 ($-N-\underline{Me}$) |
| VI-11 | $-H$ | $-Me$ | $-Me$ | $-O-CMe_3$ | 1.47 ($-C\underline{Me}_3$); 2.44 ($-N-\underline{Me}$) |

[a] $^1$H-NMR (400 MHz, CDCl$_3$, δ) in ppm; in each case singlets.

We claim:

1. A method for combating pathogenic endoparasites in a human or animal which comprises administering an endoparasiticidally effective amount of an open-chain hexadepsipetide of the formula

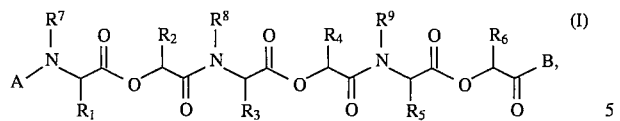

(I)

in which represents hydrogen, alkyl, aralkyl or an acyl radical of the formula —CO—$R^{10}$ in which $R^{10}$ represents straight-chain, branched alkyl, aralkyl, alkoxy or arylalkoxy having up to 6 carbon atoms in the alkyl moiety, $R^1$, $R^3$ and $R^5$ independently of one another represent hydrogen, straight-chain or branched alkyl having up to 8 carbon atoms, hydroxyalkyl, alkanoyloxyalkyl, alkoxy-alkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidino-alkyl which is optionally substituted by one or two benzyloxycarbonyl radicals or by one, two, three or four alkyl radicals, or represent alkoxycarbonylaminoalkyl, 9-fluorenylmethoxycarbonly(Fmoc)-aminoalkyl, alkenyl, cycloalkyl, cycloalkylalkyl, optionally substituted aryl, optionally substituted hetarylmethyl and optionally substituted arylalkyl, wherein the substituents are selected from the group consisting of halogen, hydroxyl, alkyl, alkoxy, nitro, and a radical —$NR^{11}R^{12}$, where $R^{11}$ and $R^{12}$ independently of one another represent hydrogen or alkyl or $R^{11}R^{12}$ together with the adjacent N atom represent a carbocyclic 5-, 6- or 7-membered ring which is optionally interrupted by O, S and N wherein said 5-, 6- or 7-membered ring is optionally substituted by $C_1$–$C_4$-alkyl, $R^2$, $R^4$ and $R^6$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, hetarylmethyl and optionally substituted arylalkyl, wherein said substituents are selected from the group consisting of halogen, hydroxyl, alkyl, alkoxy, nitro, and a radical —$NR^{11}R^{12}$, where $R^{11}$ and $R^{12}$ independently of one another represent hydrogen or alkyl or $R^{11}R^{12}$ together with the adjacent N atom represent a carbocyclic 5-, 6- or 7-membered ring which is optionally interrupted by O, S and N and wherein said 5-, 6- or 7-membered ring is optionally substituted by $C_1$–$C_4$-alkyl, $R^7$, $R^8$ and $R^9$ independently of one another represent hydrogen, $C_{1-8}$-alkyl, $C_{3-6}$-cycloalkyl or aralkyl, B represents hydroxyl or alkoxy having up to 4 carbon atoms, or its optical isomer and racemates thereof to said human or animal.

2. An endoparasiticidal composition for combating pathogenic endoparasites in human or animal which comprises an endoparositicidally effective amount of an open-chain hexadepsipetide of the formula

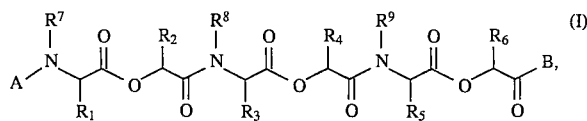

(I)

in which

A represents hydrogen, alkyl, aralkyl or an acyl radical of the formula —CO—$R^{10}$ in which $R^{10}$ represents straight-chain, branched alkyl, aralkyl, alkoxy or arylalkoxy having up to 6 carbon atoms in the alkyl moiety, $R^1$, $R^3$ and $R^5$ independently of one another represent hydrogen, straight-chain or branched alkyl having up to 8 carbon atoms, hydroxyalkyl, alkanoyloxyalkyl, alkoxy-alkyl, aryloxyalkyl, mercaptoalkyl, alkylthioalkyl, alkylsulphinyialkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidino-alkyl which is optionally substituted by one or two benzyloxycarbonyl radicals or by one, two, three or four alkyl radicals, or represent alkoxycarbonylaminoalkyl, 9-fluorenylmethoxycarbonyl(Fmoc)-aminoalkyl, alkenyl, cycloalkyl, cycloalkylalkyl, optionally substituted aryl, optionally substituted hetarylmethyl and optionally substituted arylalkyl, wherein the substituents are selected from the group consisting of substituents halogen, hydroxyl, alkyl, alkoxy, nitro, and a radical —$NR^{11}R^{12}$, wherein $R^{11}$ and $R^{12}$ independently of one another represent hydrogen or alkyl or $R^{11}R^{12}$ together with the adjacent N atom represent a carbocyclic 5-, 6- or 7-membered ring which is optionally interrupted by O, S and N wherein said 5-, 6- or 7- membered ring is optionally substituted by $C_1$–$C_4$-alkyl, $R^2$, $R^4$ and $R^6$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, hetarylmethyl and optionally substituted arylalkyl, wherein said substituents are selected from the group consisting of halogen, hydroxyl, alkyl, alkoxy, nitro, and a radical —$NR^{11}R^{12}$, where $R^{11}$ and $R^{12}$ independently of one another represent hydrogen or alkyl or $R^{11}R^{12}$ together with the adjacent N atom represent a carbocyclic 5-, 6- or 7-membered ring which is optionally interrupted by O, S and N and wherein said 5-, 6- or 7-membered ring is optionally substituted by $C_1$–$C_4$-alkyl, $R^7$, $R^8$ and $R^9$ independently of one another represent hydrogen, $C_{1-8}$-alkyl, $C_{3-6}$-cycloalkyl or aralkyl, B represents hydroxyl or alkoxy having up to 4 carbon atoms, and a pharmaceutically acceptable adjuvant, extender or surfactant.

3. A process for the preparation of endoprasiticidal compositions, characterized in that an open-chain hexadepsipeptide of the formula (I) according to claim 2 is mixed with extenders and/or surfactants.

\* \* \* \* \*

UNITED STATES PATENT AND TRADEMARK OFFICE
CERTIFICATE OF CORRECTION

PATENT NO.   : 5,529,984
DATED        : June 25, 1996
INVENTOR(S)  : Jeschke, et al.

It is certified that error appears in the above-indentified patent and that said Letters Patent is hereby corrected as shown below:

Col. 39, line 8     Before " represents " insert -- A --

Col. 40, line 16    Delete " alkylsulphinyialkyl " and substitute -- alkylsulphinylalkyl --

Signed and Sealed this

Fifth Day of November, 1996

Attest:

BRUCE LEHMAN

Attesting Officer      Commissioner of Patents and Trademarks